US009929292B2

(12) United States Patent
Dougakiuchi et al.

(10) Patent No.: US 9,929,292 B2
(45) Date of Patent: Mar. 27, 2018

(54) QUANTUM CASCADE DETECTOR

(71) Applicant: HAMAMATSU PHOTONICS K.K., Hamamatsu-shi, Shizuoka (JP)

(72) Inventors: Tatsuo Dougakiuchi, Hamamatsu (JP); Akio Ito, Hamamatsu (JP); Tadataka Edamura, Hamamatsu (JP); Kazuue Fujita, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/423,836

(22) Filed: Feb. 3, 2017

(65) Prior Publication Data
US 2017/0243994 A1 Aug. 24, 2017

(30) Foreign Application Priority Data

Feb. 18, 2016 (JP) .................................. 2016-028890
Jun. 24, 2016 (JP) .................................. 2016-125811

(51) Int. Cl.
*G01N 21/3504* (2014.01)
*H01L 31/0352* (2006.01)
(Continued)

(52) U.S. Cl.
CPC . *H01L 31/035236* (2013.01); *G01N 21/3504* (2013.01); *H01L 31/02161* (2013.01); *H01L 31/02327* (2013.01); *H01L 31/03042* (2013.01); *H01L 31/03046* (2013.01); *H01L 31/035281* (2013.01); *H01L 31/109* (2013.01); *G01N 2201/068* (2013.01); *G01N 2201/0873* (2013.01)

(58) Field of Classification Search
CPC ....... H01L 31/035236; H01L 31/02327; H01L 31/035281; H01L 31/03046; H01L 31/109; H01L 31/02161; H01L 31/03042; G01N 21/3504; G01N 2201/0873; G01N 2201/068

USPC ...................................................... 438/22, 24
See application file for complete search history.

(56) References Cited

U.S. PATENT DOCUMENTS 5,358,880 A * 10/1994 Lebby ................. H01L 33/0066
  257/E33.069
2015/0123076 A1* 5/2015 Fujita .............. H01L 31/035236
  257/20

OTHER PUBLICATIONS

F.R. Giorgetta et al., "Quantum Cascade Detectors", IEEE Journal of Quantum Electronics, vol. 45, No. 8, 2009, p. 1039-p. 1052.
(Continued)

*Primary Examiner* — Caleen Sullivan
(74) *Attorney, Agent, or Firm* — Drinker Biddle & Reath LLP

(57) ABSTRACT

A quantum cascade detector includes a semiconductor substrate; an active layer having a cascade structure; a lower cladding layer provided between the active layer and the substrate and having a lower refractive index than the active layer; a lower metal layer provided between the lower cladding layer and the substrate; an upper cladding layer provided on an opposite side to the substrate with respect to the active layer and having a lower refractive index than the active layer; and an upper metal layer provided on an opposite side to the active layer with respect to the upper cladding layer. A first end face being in a waveguide direction in a waveguide structure with the active layer, lower cladding layer, and upper cladding layer is an entrance surface for light to be detected.

9 Claims, 19 Drawing Sheets

(51) Int. Cl.
*H01L 31/0304* (2006.01)
*H01L 31/109* (2006.01)
*H01L 31/0216* (2014.01)
*H01L 31/0232* (2014.01)

(56) References Cited

OTHER PUBLICATIONS

A. Harrer et al., "Plasmonic lens enhanced mid-infrared quantum cascade detector", Applied Physics Letters, vol. 105, 2014, p. 171112-1-p. 171112-4.
B. Schwarz et al., "Monolithically integrated mid-infrared lab-on-a-chip using plasmonics and quantum cascade structures", Nature Communications, vol. 5, Art. 4085, 2014, p. 1-p. 7.

* cited by examiner

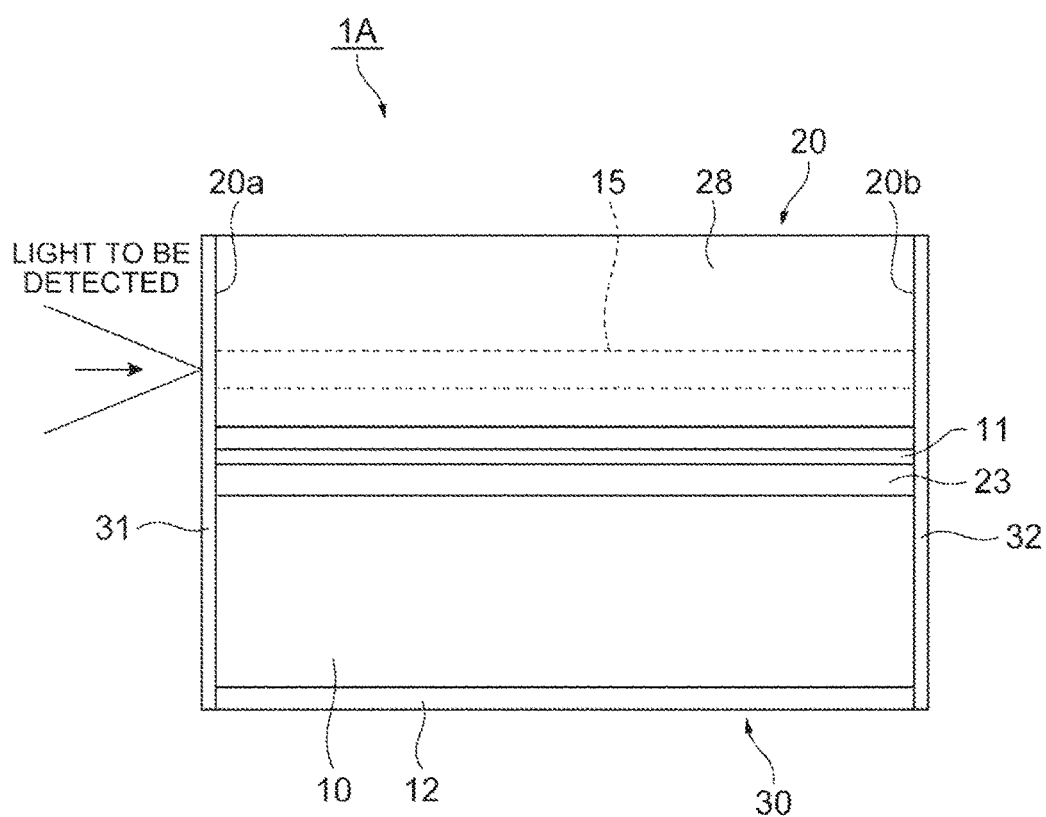

Fig.3

| SEMICONDUCTOR LAYER | | COMPOSITION | LAYER THICKNESS (nm) | DOPING |
|---|---|---|---|---|
| CONTACT LAYER 27 | | InGaAs | 250 | Si doped: $3 \times 10^{18}/cm^3$ |
| CLADDING LAYER 26 | | InP | 3000 | Si doped: $1 \times 10^{17}/cm^3$ |
| ABSORPTION REGION 17 | BARRIER LAYER 171 | InAlAs | 3.0 | undoped |
| | WELL LAYER 161 | InGaAs | 4.4 | Si doped: $5 \times 10^{17}/cm^3$ |
| TRANSPORT REGION 18 | BARRIER LAYER 172 | InAlAs | 2.5 | undoped |
| | WELL LAYER 162 | InGaAs | 0.9 | undoped |
| | 173 | InAlAs | 4.0 | undoped |
| | 163 | InGaAs | 1.3 | undoped |
| | 174 | InAlAs | 3.3 | undoped |
| | 164 | InGaAs | 1.4 | undoped |
| | 175 | InAlAs | 3.6 | undoped |
| | 165 | InGaAs | 1.5 | undoped |
| | 176 | InAlAs | 2.8 | undoped |
| | 166 | InGaAs | 2.5 | undoped |
| | 177 | InAlAs | 2.7 | undoped |
| | 167 | InGaAs | 2.8 | undoped |
| ⋮ | | | | 45 PERIODS |
| CLADDING LAYER 21 | | InP | 3000 | Si doped: $1 \times 10^{17}/cm^3$ |
| CONTACT LAYER 22 | | InAlAs | 0.2 | undoped |
| | | InGaAs | 250 | Si doped: $3 \times 10^{18}/cm^3$ |

QUANTUM CASCADE DETECTOR

BACKGROUND OF THE INVENTION

Field of the Invention

The present invention relates to a quantum cascade detector using intersubband light absorption in a quantum well structure.

Related Background Art

Since there are absorption lines corresponding to fundamental vibrations of a number of gas molecules in a mid-infrared region (for example, a region of a wavelength of 4 to 10 μm), mid-infrared light has been applied in the infrared absorption spectroscopy. In particular, when a laser light source is used as a mid-infrared light source, only an absorption line of a particular gas type is observed by using its narrow band emission line width, whereby high sensitivity absorption spectroscopy can be achieved without being disturbed by components of other gas types.

As a photodetector in a mid-infrared wavelength region, an MCT (HgCdTe) detector, an InSb detector, a quantum well infrared photodetector (QWIP), and the like have been known, and for a spectroscopic experiment for measuring weak mid-infrared light, a liquid nitrogen cooling type MCT detector or InSb detector has been mainly used. However, each of the MCT detector and the InSb detector requires application of an external voltage for driving, and noise (dark current) is generated due to the voltage application. Therefore, in these detectors, suppression of the noise has been a problem to improve S/N characteristics and sensitivity of spectroscopic measurement. In addition, the MCT detector has a problem such that it contains a toxic material, and is difficult to be used generally.

Meanwhile, in recent years, as a photodetector in the mid-infrared region, a quantum cascade detector (QCD) using a cascade structure has been proposed. The quantum cascade detector is capable of taking out photoelectric current without application of the external voltage, by controlling intersubband transitions with a design of a quantum well structure in an active layer. For this reason, the quantum cascade detector does not generate a noise component caused by the external voltage, and is expected as an extremely low-noise photodetector. In addition, the quantum cascade detector can be configured by general semiconductor materials, so that a problem of a toxic material such as in the MCT detector does not occur (for example, see Non Patent Documents 1 to 3).

Non Patent Document 1: F. R. Giorgetta et al., "Quantum Cascade Detectors", IEEE Journal of Quantum Electronics Vol. 45 No. 8 (2009) pp. 1039-1052

Non Patent Document 2: A. Harrer et al., "Plasmonic lens enhanced mid-infrared quantum cascade detector", Appl. Phys. Lett. Vol. 105 (2014) pp. 171112-1-171112-4

Non Patent Document 3: B. Schwarz et al., "Monolithically integrated mid-infrared lab-on-a-chip using plasmonics and quantum cascade structures", Nat. Commun. Vol. 5 Art. 4085 (2014) pp. 1-7

SUMMARY OF THE INVENTION

The above-described quantum cascade detector has polarization dependency in a response to light to be detected entering the detector due to a selection rule of intersubband optical transition, and this is a constraint in light detection. Specifically, since the quantum cascade detector has light sensitivity only for polarized light (TM polarized light) oscillating along a lamination direction (growth direction) of semiconductor layers constituting the quantum well structure and cannot have a wide light receiving area, efficient entering of light to the detector and light detection with high sensitivity are difficult.

For this problem, in a configuration described in Non Patent Document 1, a substrate end face is polished to 45° and light is caused to enter from the polished surface, and multiple reflection inside the substrate is used to detect the light in the active layer. However, in this configuration, since there are many components not contributing to detection sensitivity of the light entering the substrate, it is difficult to achieve efficient light detection.

In a configuration described in Non Patent Document 2, light is caused to enter a metal periodic structure formed on the same substrate as the quantum cascade detector, and plasmons are excited and propagated, and then light caused by the plasmons is detected by the quantum cascade detector. However, in this configuration, there are problems that an entire device structure including the quantum cascade detector and the metal periodic structure is complicated, and manufacturing the detector is not easy.

In a configuration described in Non Patent Document 3, a quantum cascade laser and a quantum cascade detector are arranged to face each other on the same substrate. However, in this configuration, since both functions of the laser and the detector are implemented, the structure of the active layer cannot be optimized for either of the laser or the detector.

The present invention has been made in order to solve the above problem, and an object thereof is to provide a quantum cascade detector capable of detecting light to be detected with high efficiency.

In order to achieve the above object, a quantum cascade detector according to the present invention includes: (1) a semiconductor substrate; (2) an active layer provided on the semiconductor substrate and having a cascade structure in which absorption regions and transport regions are alternately stacked in the form of a multistage lamination of unit laminate structures each of which includes n (where n is an integer of 3 or more) quantum well layers including a first well layer serving as an absorption well layer and n quantum barrier layers, the absorption region including the first well layer and detecting light to be detected by intersubband absorption, the transport region transporting electrons excited by the intersubband absorption; (3) a lower cladding layer provided between the active layer and the semiconductor substrate and having a lower refractive index than the active layer; (4) a lower metal layer provided between the lower cladding layer and the semiconductor substrate; (5) an upper cladding layer provided on an opposite side to the semiconductor substrate with respect to the active layer and having a lower refractive index than the active layer; and (6) an upper metal layer provided on an opposite side to the active layer with respect to the upper cladding layer, wherein, (7) of a first end face and a second end face being in a waveguide direction in a waveguide structure with the active layer, the lower cladding layer, and the upper cladding layer, the first end face is an entrance surface for the light to be detected.

In the above-described quantum cascade detector, the active layer to be used for detecting the light to be detected is provided with the lower cladding layer being below the active layer and between the active layer and the substrate, and the upper cladding layer above the active layer, and the first end face is the entrance surface for the light to be detected, the first end face being one end in the waveguide structure with the active layer, and the lower, upper cladding layers. According to this configuration, the light to be detected entering from the first end face can be guided along the active layer with the waveguide structure, and the light to be detected can be efficiently absorbed and detected in the active layer.

Further, in this configuration, the above waveguide structure is provided with the lower metal layer being below the lower cladding layer and between the lower cladding layer and the substrate, and the upper metal layer above the upper cladding layer. In this way, the waveguide structure with the active layer and the lower, upper cladding layers is configured to be sandwiched by the lower metal layer and the upper metal layer, whereby the light receiving area in the detector is limited, and a specific detectivity can be improved. From the above, according to the quantum cascade detector of the above configuration, the light to be detected can be suitably detected with high efficiency.

According to the quantum cascade detector of the present invention, the active layer to be used for detecting the light to be detected is provided with the lower cladding layer between the active layer and the substrate, and the upper cladding layer above the active layer, the first end face is set to be the entrance surface for the light to be detected in the waveguide structure by the active layer and the lower, upper cladding layers, and the detector is provided with the lower metal layer between the lower cladding layer and the substrate, and the upper metal layer above the upper cladding layer, whereby the light to be detected can be suitably detected with high efficiency.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 2 is a side view showing a configuration of the quantum cascade detector shown in FIG. 1.

FIG. 3 is a table showing an example of a semiconductor laminate structure in the quantum cascade detector.

DESCRIPTION OF THE EMBODIMENTS

Figure 1:
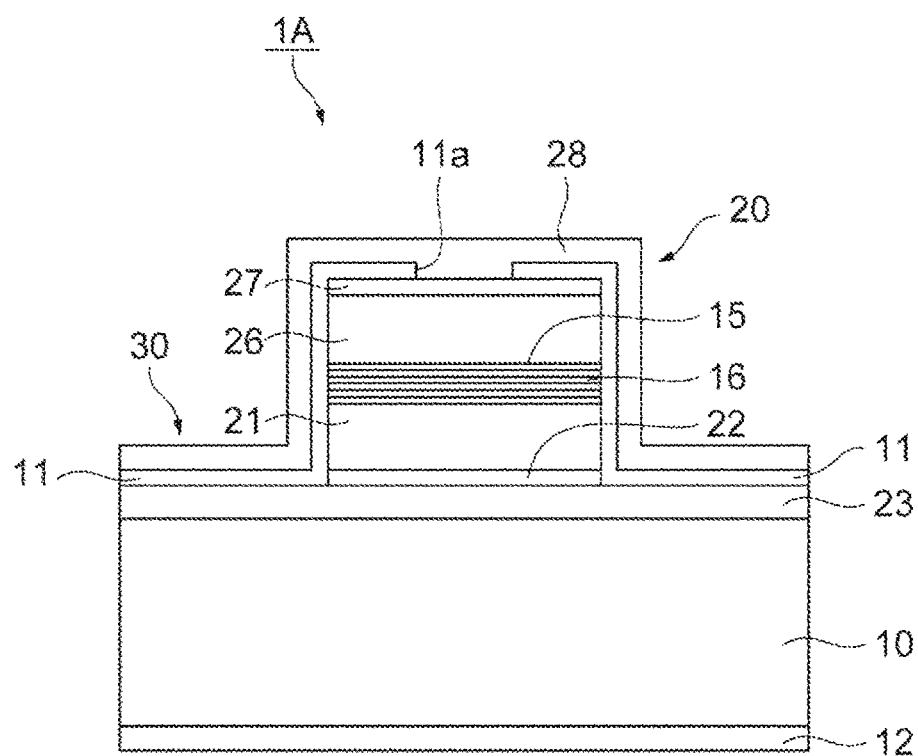
FIG. 1 is a front cross-sectional view showing a configuration of an embodiment of a quantum cascade detector.

Hereinafter, an embodiment of a quantum cascade detector according to the present invention will be described in detail with reference to the drawings. In the description of the drawings, the same elements will be denoted by the same reference signs, without redundant description. The dimensional ratios in the drawings are not always coincident with those in the description.

FIG. 1 is a front cross-sectional view showing a configuration of an embodiment of a quantum cascade detector. FIG. 2 is a side view showing the configuration of the quantum cascade detector shown in FIG. 1. A quantum cascade detector 1A according to the present embodiment is a photodetector for detecting light by using light absorption due to intersubband electron excitation in a semiconductor quantum well structure. The quantum cascade detector 1A is configured to include a semiconductor substrate 10, and an active layer 15 formed on the substrate 10.

The active layer 15 has a cascade structure in which an absorption region (light absorption layer) to be used for absorption and detection of light, and a transport region (electron transport layer) to be used for transport of electrons being carriers, are stacked alternately in multiple stages. Specifically, in the active layer 15, when n is an integer of 3 or more, a unit laminate structure 16 of one period (see FIG. 1) is a semiconductor laminate structure including n quantum well layers including a first well layer serving as an absorption well layer, and n quantum barrier layers, and a cascade structure is formed in which the absorption regions and the transport regions are alternately stacked in the form of a multistage lamination of the unit laminate structures 16, the absorption region including the first well layer and detecting light to be detected by intersubband absorption, and the transport region transporting electrons excited by intersubband absorption. The configuration of the unit laminate structure 16 included in the active layer 15 is described later specifically.

The active layer 15 is provided with a lower cladding layer 21 formed to be adjacent to the active layer 15 and having a lower refractive index than that of the active layer 15, below the active layer 15 and between the active layer 15 and the semiconductor substrate 10. A lower contact layer 22 is provided below the lower cladding layer 21. A lower metal layer 23 is provided between the lower cladding layer 21, the lower contact layer 22 and the semiconductor substrate 10.

The active layer 15 is provided with an upper cladding layer 26 formed to be adjacent to the active layer 15 and having a lower refractive index than that of the active layer 15, above the active layer 15 and on an opposite side to the semiconductor substrate 10. An upper contact layer 27 is provided above the upper cladding layer 26. An upper metal layer 28 is provided on an opposite side to the active layer 15 with respect to the upper cladding layer 26 and the upper contact layer 27.

From the above, on the semiconductor substrate 10, a laminate structure is formed by the lower metal layer 23, the lower contact layer 22, the lower cladding layer 21, the active layer 15, the upper cladding layer 26, the upper contact layer 27, and the upper metal layer 28. Of a first end face 20a and a second end face 20b (see FIG. 2) being in a waveguide direction in a waveguide structure of light by the active layer 15, the lower cladding layer 21, and the upper cladding layer 26, the first end face 20a is an entrance surface at which the light to be detected enters, the light being a detection object in the detector 1A. As each of the first end face 20a and the second end face 20b, a cleavage plane is preferably used. A lower electrode layer 12 made of a metal layer is formed on a rear surface being the opposite side to the active layer 15 of the semiconductor substrate 10.

In the present embodiment, the quantum cascade detector 1A is configured in a mesa structure having a base portion 30 including the semiconductor substrate 10; and a mesa portion 20 provided on the base portion 30 and including the active layer 15, and extending in a stripe shape in the waveguide direction in the above waveguide structure. In the configuration example shown in FIG. 1, the semiconductor substrate 10 and the lower metal layer 23 constitute the base portion 30, and the lower contact layer 22, the lower cladding layer 21, the active layer 15, the upper cladding layer 26, and the upper contact layer 27 constitute the mesa portion 20.

On the base portion 30 and the mesa portion 20, an insulating layer 11 is formed to cover both side surfaces and an upper surface of the mesa portion 20, and an upper surface of the lower metal layer 23 exposed on the substrate 10. The upper metal layer 28 is faulted on the insulating layer 11. In the insulating layer 11, an opening (contact hole) 11a is formed on the upper surface of the mesa portion 20, and the upper metal layer 28 is in contact with the upper contact layer 27 via the opening 11a. In this configuration, the upper metal layer 28 serves as an upper electrode layer.

In the configuration example shown in FIG. 2, for the waveguide structure with the active layer 15 and the lower, upper cladding layers 21, 26, an antireflection film (low reflection film) 31 configured to reduce reflectance for light of the wavelength of the light to be detected is formed on the first end face 20a to be the entrance surface in the waveguide structure. Further, a reflection film (high reflection film) 32 configured to increase reflectance for light of the wavelength of the light to be detected is formed on the second end face 20b being the opposite side to the first end face 20a in the waveguide structure, and the second end face 20b is a reflection surface for reflecting the light to be detected.

Effects of the quantum cascade detector 1A according to the present embodiment will be described.

In the quantum cascade detector 1A shown in FIG. 1, FIG. 2, the active layer 15 to be used for detecting the light to be detected is provided with the lower cladding layer 21 below the active layer 15 and between the active layer and the substrate 10, and the upper cladding layer 26 above the active layer 15, and further, the first end face 20a is the entrance surface for the light to be detected, the first end face being one end in the waveguide structure by the active layer 15 and the lower, upper cladding layers 21, 26. According to this configuration, the light to be detected entering from the first end face 20a can be guided along the active layer 15 in the waveguide structure using the cladding layers 21, 26, and the light to be detected can be efficiently absorbed and detected in the active layer 15.

Further, in this configuration, the above waveguide structure is provided with the lower metal layer 23 below the lower cladding layer 21 and between the lower cladding layer and the substrate 10, and the upper metal layer 28 above the upper cladding layer 26. In this way, the waveguide structure with the active layer 15 and the lower, upper cladding layers 21, 26 is configured to be sandwiched by the lower metal layer 23 and the upper metal layer 28, whereby an area of a light receiving portion of the detector 1A on the entrance surface 20a is limited by the metal layers 23, 28, and a specific detectivity can be improved. From the above, according to the quantum cascade detector 1A of the above configuration, the light to be detected can be suitably detected with high efficiency. The quantum cascade detector 1A of this configuration can be suitably applied to detection of light of a mid-infrared region of, for example, a wavelength of 4 to 10 μm.

In the above embodiment, the quantum cascade detector 1A is configured in the mesa structure having the base portion 30 including the semiconductor substrate 10, and the mesa portion 20 provided on the base portion 30, including the active layer 15, and extending in a stripe shape in the waveguide direction in the waveguide structure. According to this configuration, the waveguide structure with the active layer 15 and the cladding layers 21, 26 can be suitably configured along a direction in which the mesa portion 20 extends.

In the above embodiment, the antireflection film 31 for reducing reflectance for the light to be detected (for example, the reflectance for the light of the wavelength at which detection sensitivity of the detector 1A is the highest) is formed on the first end face 20a being the entrance surface for the light to be detected in the waveguide structure. According to this configuration, incident efficiency is improved of the light to be detected from the entrance surface 20a to the inside of the quantum cascade detector 1A, whereby detection efficiency of the light in the detector 1A can be improved. The antireflection film 31 is preferably configured to have reflectance of 28% or less for the light of the wavelength of the light to be detected.

In the above embodiment, the reflection film 32 for increasing reflectance for the light to be detected is formed on the second end face 20b being a reflection surface for the light to be detected in the waveguide structure. According to this configuration, the light to be detected guided from the entrance surface through the waveguide structure and reaching the reflection surface 20b is returned to the inside of the quantum cascade detector 1A again, whereby detection efficiency of the light in the detector 1A can be improved. The reflection film 32 is preferably configured to have reflectance of 95% or more for the light of the wavelength of the light to be detected.

Here, as for the layer thickness of each semiconductor layer constituting the quantum cascade detector 1A, each of the lower cladding layer 21 and the upper cladding layer 26 preferably has a layer thickness of 2 µm or more and 10 µm or less. The active layer 15 preferably has a layer thickness of 1 µm or more. According to these configurations, it is possible to suitably achieve the waveguide structure for the light to be detected by the active layer 15 and the cladding layers 21, 26, a light confinement structure in the waveguide, and the like.

In each of the lower cladding layer 21 and the upper cladding layer 26, the doping density of impurities (n type impurities) is preferably $5 \times 10^{16}$ cm$^{-3}$ or more and $2 \times 10^{17}$ cm$^{-3}$ or less. According to this configuration, by the setting of the doping density in the cladding layers 21, 26, series resistance in the detector 1A can be reduced, and loss of light in the cladding layers 21, 26 can be suppressed.

In the active layer 15, the doping density of impurities (n type impurities) is preferably $1 \times 10^{17}$ cm$^{-3}$ or more and $9 \times 10^{17}$ cm$^{-3}$ or less. According to this configuration, it is possible to suitably achieve the waveguide structure with the active layer 15 and cladding layers 21, 26, the light confinement structure in the waveguide, and a light detection structure in the active layer 15. The configuration conditions of the quantum cascade detector 1A such as the layer thickness of each of the semiconductor layers and the doping density of impurities are specifically described later.

Figure 4:
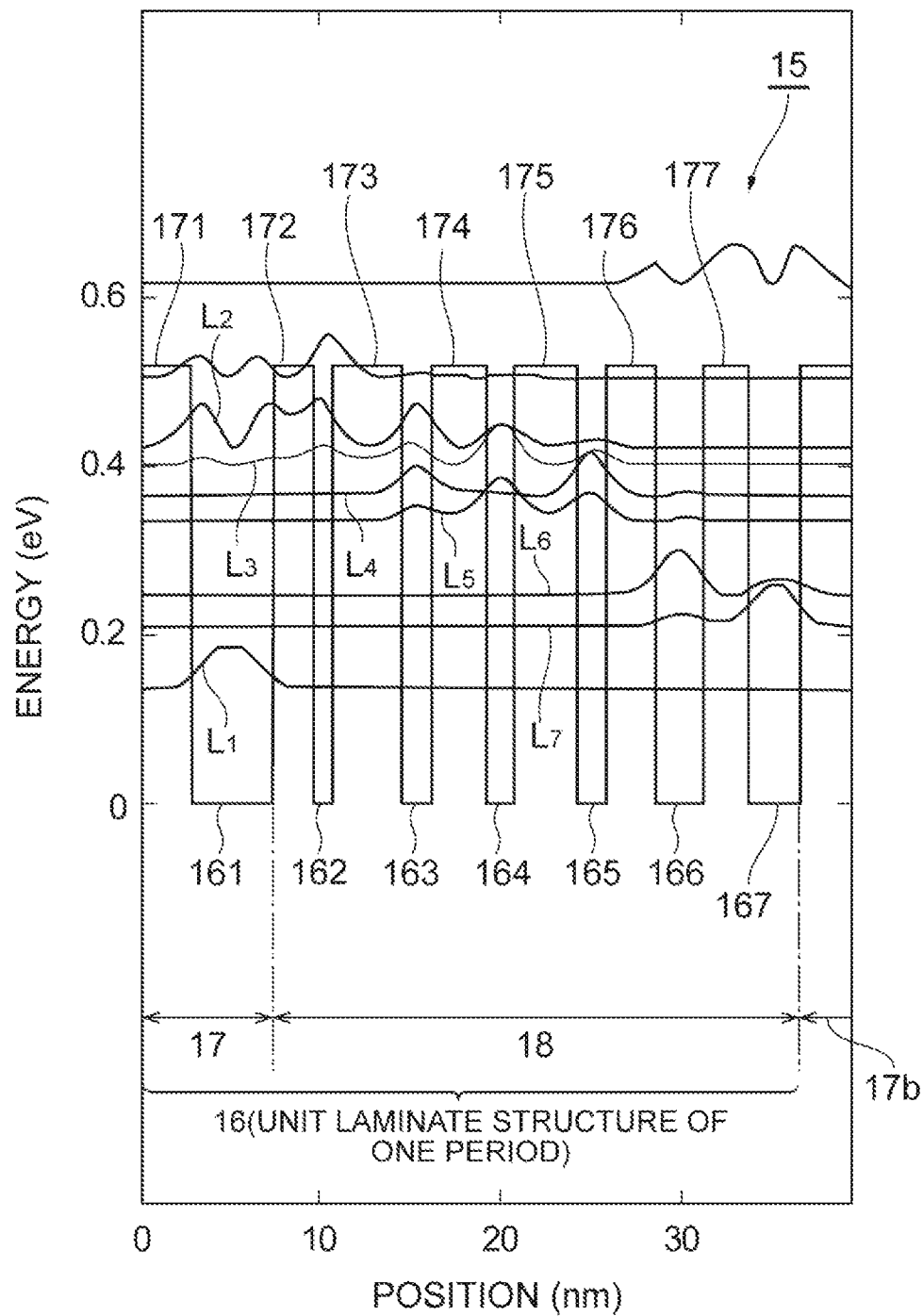
FIG. 4 is a diagram showing an example of a configuration of a unit laminate structure constituting an active layer in the quantum cascade detector.

The configuration of the quantum cascade detector 1A according to the above embodiment will be described, with a specific example of a device structure including the quantum well structure in the active layer 15. FIG. 3 is a table showing an example of the semiconductor laminate structure in the quantum cascade detector 1A. FIG. 4 is a diagram showing an example of the configuration of the unit laminate structure 16 constituting the active layer 15 in the quantum cascade detector 1A.

In the present configuration example, an example is shown in which the quantum well structure in the active layer 15 is designed to have an energy interval of 290 meV between the detection lower level and the detection upper level that gives a peak of a sensitivity spectrum of light detection, and have detection sensitivity for the light of a wavelength λ=4.5 µm included in the mid-infrared region. However, the detection wavelength in the quantum cascade detector 1A of the above embodiment is not limited to 4.5 µm, and may be arbitrarily set as necessary. For example, the detection wavelength may be set in a wavelength region of 4 to 10 µm in the mid-infrared region.

FIG. 4 shows the quantum well structure and subband level structure in a part of the multistage repetition structure of the unit laminate structures 16 each of which includes an absorption region 17 and a transport region 18 in the active layer 15. The device structure with the semiconductor laminate structure in the quantum cascade detector 1A can be formed by crystal growth with the molecular beam epitaxy (MBE) method, or the metal organic chemical vapor deposition (MOCVD) method, for example.

In the semiconductor laminate structure of the quantum cascade detector 1A according to the present configuration example, an n type InP substrate is used as the semiconductor substrate 10 in the configuration shown in FIG. 1, FIG. 2. As shown in FIG. 1 and FIG. 3, the device structure of the quantum cascade detector 1A is formed on the InP substrate 10 by sequentially stacking the lower contact layer 22 configured by an InGaAs layer of a thickness of 250 nm and an InAlAs layer of a thickness of 0.2 nm, the InP lower cladding layer 21 of a thickness of 3000 nm, the active layer 15 in which the unit laminate structures 16 each including the absorption region 17 and the transport region 18 are stacked 45 periods, the InP upper cladding layer 26 of a thickness of 3000 nm, and the InGaAs upper contact layer 27 of a thickness of 250 nm.

The active layer 15 in the present configuration example is configured by a multi-period lamination of the unit laminate structures 16 each of which includes the absorption region 17 and the transport region 18. The number of lamination periods of the unit laminate structure 16 in the active layer 15 can be set to, for example, 10 to 50 periods, and is set to 45 periods in the present configuration example, as described above. The unit laminate structure 16 of one period is configured as a quantum well structure in which seven quantum well layers 161 to 167, and seven quantum barrier layers 171 to 177 are alternately stacked, as shown in FIG. 3, FIG. 4.

Of these semiconductor layers of the unit laminate structure 16, each of the quantum well layers 161 to 167 is configured by an InGaAs layer. Each of the quantum barrier layers 171 to 177 is configured by an InAlAs layer. Thus, the active layer 15 in the present configuration example is configured by an InGaAs/InAlAs quantum well structure. The layer thicknesses and the like of the well layers, barrier layers constituting the active layer 15 are shown in FIG. 3.

In this unit laminate structure 16, the first barrier layer 171 and the first well layer 161 constitute the absorption region 17 for detecting light by intersubband absorption. The second to seventh barrier layers 172 to 177 and the second to seventh well layers 162 to 167 constitute the transport region 18 for transporting electrons excited by intersubband absorption to an absorption region 17b of the next period. In the first well layer 161 serving as an absorption well layer for absorbing the light to be detected, Si being an n type impurity is doped with a doping density of $5 \times 10^{17}$ cm$^{-3}$ in order to supply electrons being carriers.

In the present configuration example, as shown in FIG. 3, Si being the n type impurity is similarly doped with a doping density of $1 \times 10^{17}$ cm$^{-3}$ in each of the lower cladding layer 21 and the upper cladding layer 26. Si being the n type impurity is doped with a doping density of $3 \times 10^{18}$ cm$^{-3}$ in each of the InGaAs layer of the lower contact layer 22 and the upper contact layer 27.

In this configuration, the unit laminate structure 16 has a detection lower level L1 and a detection upper level L2 contributing to light absorption in the absorption region 17, and a plurality of transport levels L3 to L7 contributing to electron transport in the transport region 18, as conduction band subband levels to be used for light detection, in the subband level structure shown in FIG. 4.

When light of a wavelength λ enters the active layer 15 having the unit laminate structures 16, electrons existing in the detection lower level L1 are excited to the detection upper level L2 by intersubband absorption. The electrons excited to the upper level L2 are transported and extracted to the detection lower level L1 in the absorption region 17b of the subsequent stage via a transport level structure including the plurality of transport levels in the transport region 18. Electron excitation by light absorption, relaxation and transport of excited electrons, and extraction of the electrons to the unit laminate structure of the next period are repeated in the plurality of unit laminate structures 16 constituting the active layer 15, whereby cascade light absorption occurs in the active layer 15. Then, a current generated by this is taken out as a signal, and the amount of the current is measured, whereby incident light is detected.

An example will be described of a method for manufacturing the quantum cascade detector 1A according to the above embodiment. The quantum cascade detector 1A having the laminate structure in which the active layer 15 is provided with the cladding layers 21, 26 and the metal layers 23, 28, as described above, can be manufactured by substrate lamination, for example.

The laminate structure and the active layer structure in the quantum cascade detector 1A are formed by performing epitaxial growth of each layer sequentially by using the MBE method, the MOCVD method, or the like. First, a Si doped InGaAs contact layer, a Si doped InP cladding layer, an active layer having an InGaAs/InAlAs quantum well structure, a Si doped InP cladding layer, and a Si doped InGaAs contact layer are caused to grow on an InP substrate (first substrate), and further thereon, a first metal layer made of Au (gold) of a thickness of 0.5 μm to 1.0 μm is deposited.

Next, a second metal layer made of Au of a thickness of 0.5 μm to 1.0 μm is deposited on an n type InP substrate (second substrate) to be the semiconductor support substrate 10, and the first metal layer on the first substrate and the second metal layer on the second substrate are brought into contact with each other and subjected to heat treatment with a moderate load, whereby the two substrates are bonded together. The first, second metal layers bonded become the lower metal layer 23 on the substrate 10. Here, the metal material to be used for the lower, upper metal layers is not limited to Au described above, and another metal material may be used such as Cu (copper), or Al (aluminum) that can be deposited, for example.

After that, the first substrate used for growth of the semiconductor laminate structure is removed by selective chemical etching, and further, for example, a stripe-shaped mesa structure (see FIG. 1) of a width of 50 μm is formed by wet etching or dry etching. The etching is performed under a condition in which the etching reaches the lower metal layer 23 being a bonding portion of the substrate lamination, or stops in the lower contact layer 22. Further, the insulating layer 11 made of an insulating material such as SiN is formed, and the opening 11a is formed, and the upper metal layer 28 made of Au or the like and to be the upper electrode layer is formed by vapor deposition and plating.

Subsequently, the rear surface of the InP substrate 10 is polished so that the thickness of the substrate 10 is, for example, 150 μm, and the lower electrode layer 12 is formed for taking out the current, on the substrate rear surface. The lower electrode layer 12 is formed, for example, by performing vapor deposition of and making an alloy with Ti and Au/Ge/Au. Finally, cleavage is performed so that the device length is, for example, 500 μm, whereby the quantum cascade detector 1A is manufactured. The cleavage planes at this time are respectively the first end face (entrance surface) 20a and the second end face (reflection surface) 20b being in the waveguide direction in the waveguide structure with the active layer 15 and the cladding layers 21, 26 (see FIG. 2).

On the second end face 20b of the waveguide structure, the reflection film (high reflection coat) 32 is formed whose reflectance is 95% or more for the light of the wavelength of the light to be detected. Thus, the light to be detected entering from the first end face 20a to the active layer 15 and propagating through the inside is reflected by the reflection film 32, whereby a propagation distance of the light inside the detector 1A can be made twice as long as the device length.

Further, on the first end face 20a, to suppress reflection at the cleavage plane, the antireflection film (antireflection coat) 31 is formed whose reflectance is 28% or less for the light of the wavelength of the light to be detected. Here, when a refractive index of the semiconductor material is $n_1$ and a refractive index of the air is $n_0$, reflectance for light at the cleavage plane can be obtained by $(n_1-n_0)^2/(n_1+n_0)^2$. In the above-described configuration example, when the refractive index of InGaAs/InAlAs is $n_1=3.3$, and the refractive index of the air is $n_0=1$, the reflectance at the cleavage plane is 28.6%. Therefore, the antireflection film 31 is formed whose reflectance described above is 28% or less, whereby reflection of light at the cleavage plane can be suppressed.

As for the reflection film 32 on the second end face 20b, for example, a configuration can be used in which a material such as insulating $Al_2O_3$, $SiO_2$, or $CeO_2$, and Au are deposited on the end face 20b. As the reflection film 32, a dielectric multilayer film can be used in which a low refractive index material such as $Al_2O_3$, $SiO_2$, $CeO_2$, or ZnS, and a high refractive index material such as Ge are alternately stacked. As for the antireflection film 31 on the first end face 20a, for example, a configuration can be used in which $Al_2O_3$ is deposited to have a thickness of 0.78 μm. The above thickness is a value in which ¼ of the wavelength 4.5 μm is further divided by the refractive index 1.44 of $Al_2O_3$. As the antireflection film 31, a single layer film by another dielectric material, or a dielectric multilayer film by similar materials as the reflection film 32 can be used.

Figure 5:
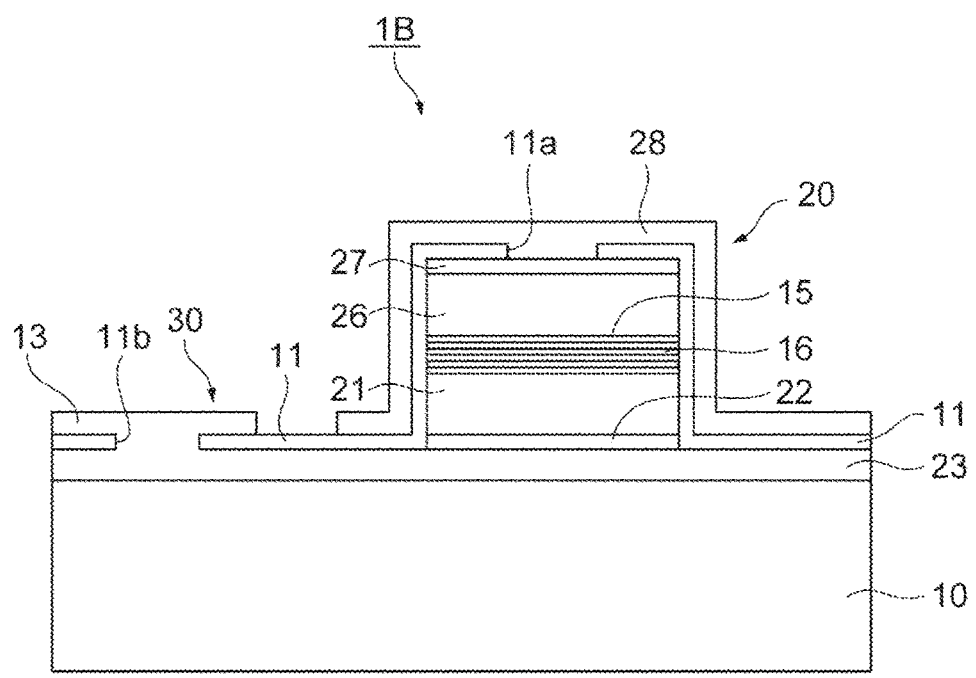
FIG. 5 is a front cross-sectional view showing a configuration of another embodiment of the quantum cascade detector.

The configuration of the quantum cascade detector will be further described. FIG. 5 is a front cross-sectional view showing a configuration of another embodiment of the quantum cascade detector. A quantum cascade detector 1B according to the present embodiment has a configuration similar to the quantum cascade detector 1A shown in FIG. 1, FIG. 2, but is different in that an opening 11b is provided on the lower metal layer 23 in addition to the opening 11a in the insulating layer 11, and that a lower electrode layer 13 is provided on the insulating layer 11 instead of the lower electrode layer 12 on the rear surface of the substrate 10.

In the configuration example shown in FIG. 5, the opening (contact hole) 11b is formed on the upper surface of the lower metal layer 23 in the insulating layer 11. A part of the upper metal layer 28 formed on the insulating layer 11 is electrically insulated from the metal layer 28 by partially removing the metal material, and the metal layer portion insulated is in contact with the lower metal layer 23 via the opening 11b and becomes the lower electrode layer 13. As for formation of the contact hole in this configuration and partial removal of the metal layer made of Au or the like, a method can be used in which a resist is patterned by photolithography, and vapor deposition of SiN, Au, and the like are performed and then the resist is removed, for example.

Specific configuration conditions and the like of the quantum cascade detector according to the above embodiment will be further described. First, a relationship will be described between the number of lamination periods of the unit laminate structure 16 in the active layer 15, noise in the detector 1A, confinement of light in the active layer 15, and the like. In a noise current $i_N$ in the quantum cascade detector 1A, thermal noise depending on only device resistance is dominant, as shown in the following Formula (1).

$$i_N = \sqrt{\frac{4k_B T \Delta f}{R}} \tag{1}$$

Here, in the above formula, $k_B$ is Boltzmann constant, T is a device temperature, $\Delta f$ is a bandwidth (here, it may be regarded as $\Delta f=1$), and R is a device resistance. From Formula (1), it can be seen that the device resistance has to be increased in order to suppress the noise current and to improve the S/N characteristic.

The device resistance in the detector 1A is in a substantially proportional relationship to the number of lamination periods of the cascade structure in the active layer 15. For this reason, the resistance of the device can be increased by increasing the number of periods of the unit laminate structures 16 in the active layer 15. Increasing the number of lamination periods in the active layer 15 in this way also contributes to an increase of a light receiving area on the first end face 20a in the waveguide structure including the active layer 15, improvement of the confinement characteristic of light when the light to be detected is guided inside the detector 1A, reduction of the loss of light, and the like.

The confinement of light in the active layer 15 will be further described in detail. The confinement of light to the active layer 15 in the quantum cascade detector 1A of the above configuration depends on configuration conditions such as the refractive index of each of the active layer 15 and the cladding layers 21, 26, the layer thicknesses of the cladding layers 21, 26, and the layer thickness of the active layer 15. In formation of the waveguide structure, it is essential that, of these conditions, the refractive index of the active layer 15 is a higher value than the refractive index of the cladding layers 21, 26. The refractive index of each semiconductor layer depends on the amount of doping of impurities in each layer, and can be obtained from a complex dielectric constant calculated on the basis of Drude model.

Figure 6:
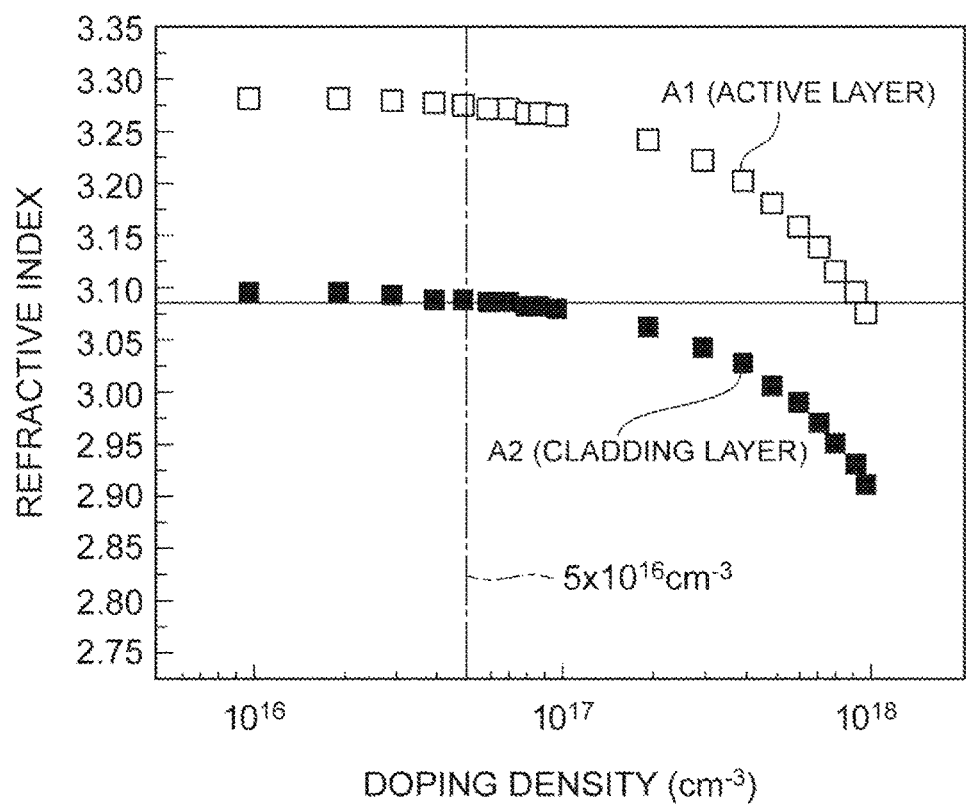
FIG. 6 is a graph showing dependency of refractive indexes of the active layer and a cladding layer on a doping density.

FIG. 6 is a graph showing dependency of refractive indexes of the active layer (InGaAs/InAlAs layer) and the cladding layer (InP layer) on the doping density. In the graph of FIG. 6, the horizontal axis shows a doping density ($cm^{-3}$) of impurities in each layer, and the vertical axis shows a refractive index. In FIG. 6, plot points A1 show a relationship between the refractive index of the active layer 15 and the doping density, and plot points A2 show a relationship between the refractive index of the cladding layers 21, 26 and the doping density.

In the waveguide structure with the active layer 15, and cladding layers 21, 26, in order to reduce the loss of light in the waveguide, the doping density of impurities in the cladding layers 21, 26 is preferably $2\times10^{17}$ $cm^{-3}$ or less. Meanwhile, in the quantum cascade detector 1A to which an external voltage is not applied, since electromotive force is small, it is necessary to suppress series resistance low in other than the active layer 15 being an photoelectric conversion portion, in order to take out photoelectric current from the electrode. When such a series resistance condition is considered, the doping density of impurities in the cladding layers 21, 26 is preferably $5\times10^{16}$ $cm^{-3}$ or more. From the above, the doping density of impurities in each of the cladding layers 21, 26 is preferably $5\times10^{16}$ $cm^{-3}$ or more and $2\times10^{17}$ $cm^{-3}$ or less, as described above.

From the graph of FIG. 6, the highest value of the refractive index of the cladding layers 21, 26, in the condition of the above doping density, is the refractive index value 3.091 in a case of the doping density of $5\times10^{16}$ $cm^{-3}$ shown by the straight line in FIG. 6. Therefore, the upper limit of the doping density of impurities in the active layer 15 is determined by the condition in which the refractive index of the active layer 15 exceeds the refractive index of the cladding layer described above. From the plot points A1 shown in FIG. 6, the upper limit of the doping density in the active layer 15 is preferably $9\times10^{17}$ $cm^{-3}$. The refractive index value of the active layer 15 in this doping density is 3.095.

Meanwhile, the lower limit of the doping density in the active layer 15 is not restricted from a viewpoint of waveguide formation, however, decreasing of free electrons contributing to photoelectric current becomes a cause of a reduction of a detection signal intensity to be generated and output by the light detection. When such a signal intensity condition is considered, the lower limit of the doping density in the active layer 15 is preferably $1\times10^{17}$ $cm^{-3}$. In a lower doping density than the lower limit value, since a change of the refractive index is small and significant improvement of the confinement characteristic of light cannot be expected, the setting of the lower limit value described above is reasonable. From the above, the doping density of impurities in the active layer 15 is preferably $1\times10^{17}$ $cm^{-3}$ or more and $9\times10^{17}$ $cm^{-3}$ or less.

Next, the layer thickness of the cladding layers 21, 26 will be described. A function of the cladding layers 21, 26 in the above configuration is to confine the light to be detected entering from the first end face 20a inside the waveguide structure with the active layer 15 and cladding layers 21, 26, and to reduce absorption loss of light in the metal layers 23, 28, and the contact layers 22, 27 having high carrier density.

As described above, when the doping density in the cladding layers 21, 26 is $5\times10^{16}$ $cm^{-3}$, and the doping density in the active layer 15 is $9\times10^{17}$ $cm^{-3}$, the refractive index difference is minimum between the active layer 15 and the cladding layers 21, 26. At this time, in the waveguide structure, the configuration condition becomes the one in which the confinement of light in the active layer 15 is the most difficult, and exudation of light to the cladding layers 21, 26 is maximized. Therefore, as for the layer thickness of the cladding layers 21, 26, in this configuration condition, a condition can be obtained capable of preventing light from reaching the contact layers 22, 27 and the metal layers 23, 28, and confining the light inside the waveguide structure. As for the wavelength of the light to be detected in the setting of the layer thickness, when the wavelength region of 4 to 10 μm in the mid-infrared region is assumed, a case can be considered of the wavelength of 10 μm in which the confinement of light is the most difficult.

Figure 7:
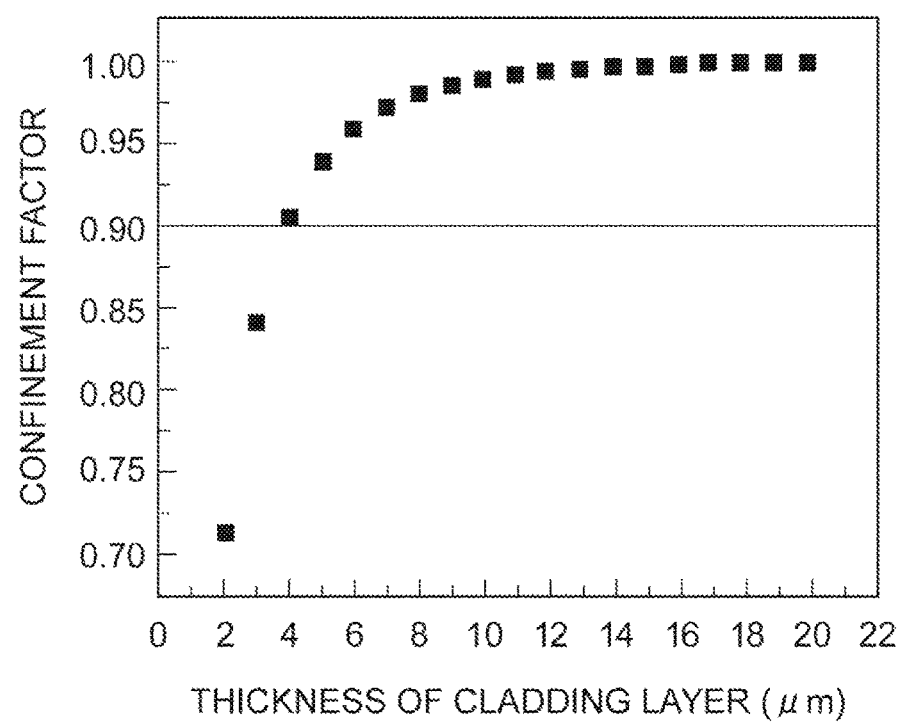
FIG. 7 is a graph showing dependency of a confinement factor of light in the cladding layer on a thickness of the cladding layer.

FIG. 7 is a graph showing dependency of a confinement factor of light in the cladding layer (InP layer) with respect to the contact layer (InGaAs layer) on the thickness of the cladding layer. In the graph of FIG. 7, the horizontal axis shows a thickness of the cladding layer (μm), and the vertical axis shows a confinement factor of light. In FIG. 7, the confinement factor of light is defined by a ratio of an integrated value of an electric field intensity in the InP cladding layer to an integrated value of an entire electric field intensity, in a case in which a one-dimensional waveguide mode in the waveguide structure is obtained.

Figure 8:
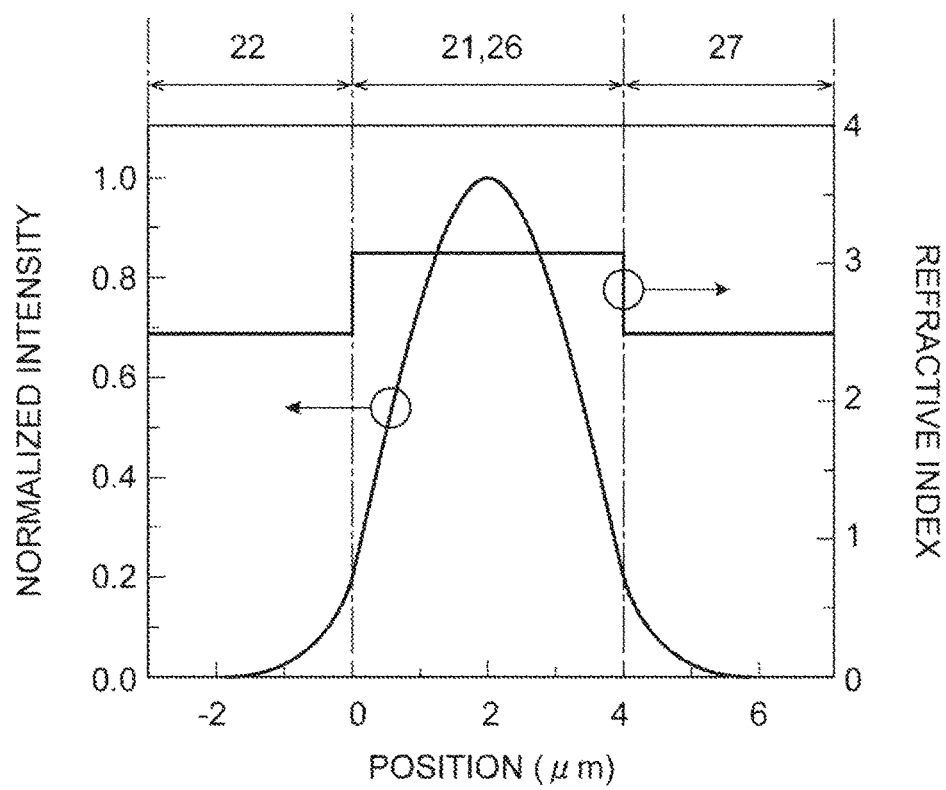
FIG. 8 is a graph showing a waveguide mode of light when the total thickness of the cladding layer is 4 μm.
Figure 9:
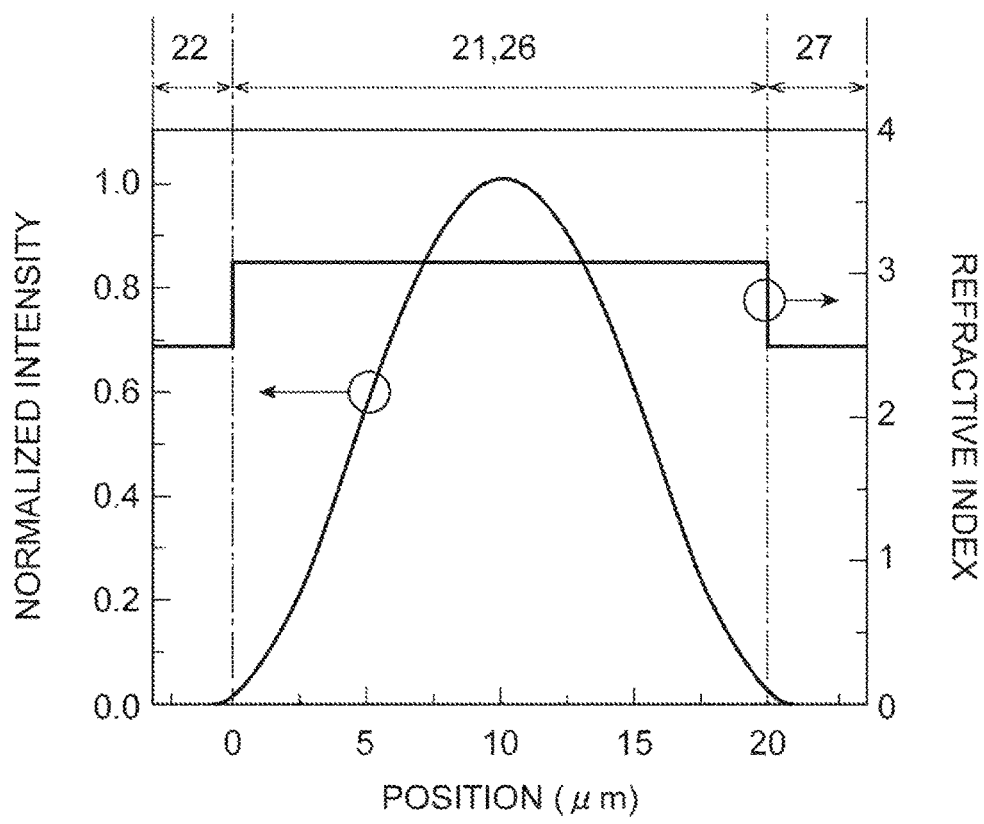
FIG. 9 is a graph showing a waveguide mode of light when the total thickness of the cladding layer is 20 μm.

FIG. 8 is a graph showing a simulation result of a waveguide mode of light when the total thickness of the InP cladding layers 21, 26 is 4 μm, for the InGaAs contact layers 22, 27, as an example of confinement of light. Similarly, FIG. 9 is a graph showing a simulation result of a waveguide mode of light when the total thickness of the cladding layers 21, 26 is 20 μm. In the graphs of FIG. 8, FIG. 9, the horizontal axis shows a position (μm), and the vertical axis shows a normalized intensity of the light to be guided, or a refractive index of each layer. Here, for calculation, the thickness of the InGaAs contact layer is 3 μm, the doping density in the contact layer is $3\times10^{18}$ $cm^{-3}$, and the refractive index is 2.5. The active layer 15 being between the cladding layers 21, 26 is not considered here.

According to the graph of FIG. 7, when the total thickness of the InP cladding layers 21, 26 is 4 µm or more, the confinement factor of light to the cladding layer is 90% or more. Therefore, the layer thickness of each of the cladding layers 21, 26 is preferably 2 µm or more. Actually, since there is the active layer 15 having a higher refractive index than that of the cladding layer, between the cladding layers 21, 26, the confinement of light to the waveguide structure becomes greater, and the absorption loss of light can be sufficiently suppressed in the contact layers 22, 27 and the metal layers 23, 28.

The upper limit of the thickness of the cladding layers 21, 26 is not particularly restricted; however, when the thickness of the cladding layer is 11 µm or more in the graph of FIG. 7, the confinement factor reaches 99% and is not changed much any longer. When such a point is considered, the layer thickness of each of the cladding layers 21, 26 is preferably 10 µm or less. From the above, the layer thickness of each of the cladding layers 21, 26 is preferably 2 µm or more and 10 µm or less.

Next, the layer thickness of the active layer 15 will be described. In the configuration in which the layer thickness of the cladding layers 21, 26 is most thinned in the above-described configuration condition, the total layer thickness of the lower cladding layer 21 and the upper cladding layer 26 is 4 µm. Meanwhile, due to diffraction limit, a spot size of light can be focused only up to about a half wavelength. Therefore, when the wavelength of the light to be detected is 10 µm, a sum of the layer thicknesses of the active layer 15 and the cladding layers 21, 26 to be the light receiving surface on the first end face 20a is preferably 5 µm or more. When such an incident condition of light is considered, the layer thickness of the active layer 15 is preferably 1 µm or more. When the wavelength of the light to be detected is less than 10 µm, since the incident condition of light and the confinement condition of light in the waveguide structure are both relaxed, the above condition for the light of a wavelength of 10 µm can be applied.

Since the layer thickness of the active layer 15 depends on the number of lamination periods of the unit laminate structures 16 in the active layer 15, the number of periods of the unit laminate structure 16 can be set so that the layer thickness of the active layer 15 is 1 µm or more. An average thickness of the unit laminate structure 16 of one period in the active layer 15 of the quantum cascade detector 1A is about 50 nm, although the thickness varies depending on the wavelength of the light to be the detection object, the specific design, or the like, in this case, the number of periods is 20 periods or more in order to make the layer thickness of the active layer 15 of 1 µm or more. As described above regarding Formula (1), this configuration condition is also suitable for increasing the resistance in the active layer 15 and suppressing the thermal noise.

Since the upper limit of the layer thickness of the active layer 15 is not particularly restricted, the layer thickness can be appropriately set to 1 µm or more. In the above configuration example, for example, the number of periods of the unit laminate structure 16 in the active layer 15 is 45 periods, whereby the layer thickness is set to 1.65 µm. As shown in FIG. 3, the layer thickness of each of the cladding layers 21, 26 is 3 µm. The doping density of impurities in the cladding layers 21, 26 is set to $1 \times 10^{17}$ cm$^{-3}$, and the doping density in the active layer 15 is set to $5 \times 10^{17}$ cm$^{-3}$.

Figure 10:
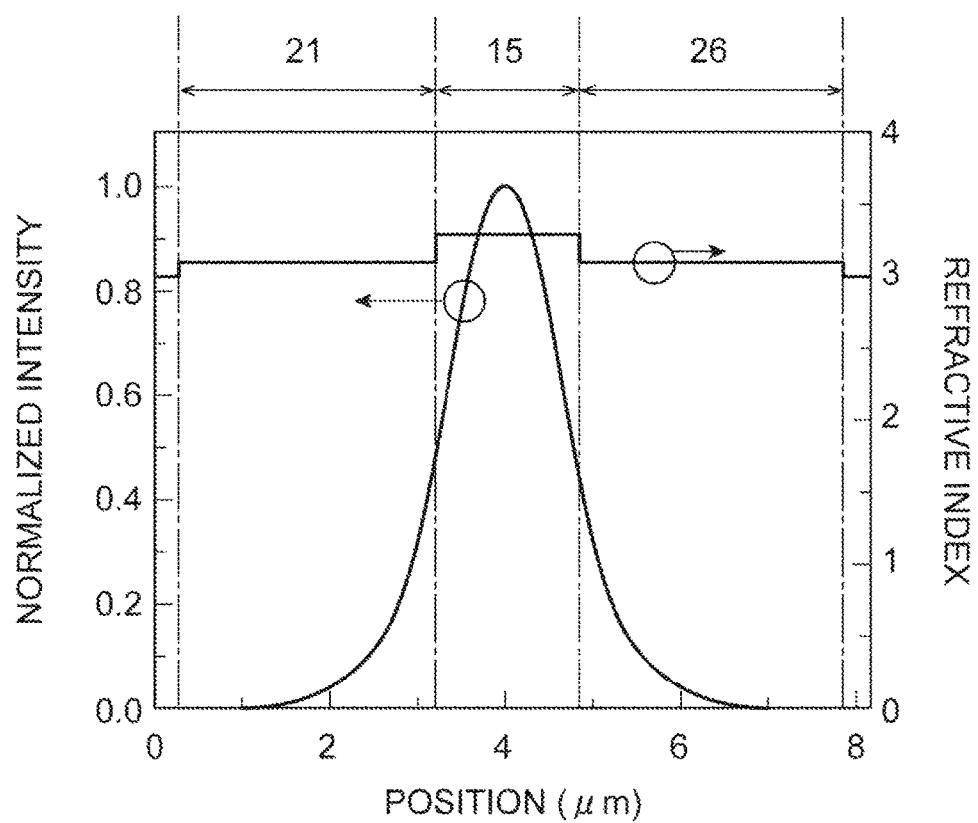
FIG. 10 is a graph showing a waveguide mode of light in a waveguide structure with the active layer and the cladding layer.

FIG. 10 is a graph showing a waveguide mode of light in the waveguide structure with the active layer 15 and cladding layers 21, 26, in the above configuration example. In the configuration example, the confinement factor of light in the active layer 15 is 0.75 corresponding to the ratio of the integrated value of the electric field intensity in the active layer to the integrated value of the entire electric field intensity.

Here, in the quantum cascade detector 1A of the configuration shown in FIG. 1, FIG. 2, incidence of the light to be detected to the waveguide structure inside the detector 1A can be performed by condensing the light with a lens on the first end face 20a being the cleavage plane on which the antireflection film 31 is formed, for example. The above device structure is used including the active layer 15, the cladding layers 21, 26, and the metal layers 23, 28, whereby the light entering from the first end face 20a can be efficiently converted to a current.

That is, with the cladding layers 21, 26 sandwiching the active layer 15 from the top and bottom, a spatial distance can be increased between the active layer 15 being the photoelectric conversion portion and the contact layers 22, 27 to which impurities are doped at a high density. Thus, the light entering the inside of the waveguide structure is prevented from being absorbed by free carriers in the contact layers 22, 27, and the light to be detected is guided inside the active layer 15 sandwiched by the cladding layers 21, 26, whereby the amount of light contributing to photoelectric conversion can be increased.

The light guided inside the active layer 15 and reaching the second end face 20b is reflected by the reflection film 32 and generates photoelectric current while being further guided inside the active layer 15. This means that the device length of the detector 1A can be shorten to ½ while keeping the detection signal intensity. Such shortening of the device length also contributes to an increase of the device resistance due to device size reduction, and is also effective in reduction of the noise current shown in Formula (1).

In the above-described configuration example, the number of periods of the unit laminate structure 16 in the active layer 15 is set to 45 periods, whereby the layer thickness of the active layer 15 is 1.65 µm. Thus, the confinement factor for the light entering the active layer 15 can be increased, and the thermal noise can be suppressed due to the increase of the device resistance in the detector 1A.

According to the above configuration having the metal layers 23, 28 that can be formed by the substrate lamination or the like, the light receiving portion in the first end face 20a is limited only to the active layer 15, and the cladding layers 21, 26 sandwiching the active layer. Thus, the light receiving area in the detector 1A can be sufficiently reduced, and a specific detectivity D* can be increased.

A relationship will be described between the light receiving area in the quantum cascade detector 1A and the specific detectivity D*. The specific detectivity D* of the detector 1A can be represented by the following Formula (2).

$$D^* = \frac{v_s}{v_n} \cdot \frac{1}{P\sqrt{A}} \cdot \sqrt{\Delta f} \quad (2)$$

Here, in the above formula, $v_s$ is an output signal voltage, $v_n$ is a noise voltage (in the quantum cascade detector, the product of the noise current shown in Formula (1) and the device resistance), P is an energy of incident light per unit area, A is the light receiving area, and $\Delta f$ is a bandwidth of the noise (here, it may be regarded as $\Delta f = 1$).

From Formula (2) above, it can be seen that, when each of the voltages $v_s$, $v_n$ and the energy P of the incident light is constant, the specific detectivity D* depends on the light receiving area A, and the specific detectivity D* is increased as the light receiving area A is decreased.

In the device structure of the quantum cascade detector 1A described above, the photoelectric conversion portion is the active layer 15, and an entrance portion of the light is originally limited to a cross section of the active layer 15 in the first end face 20a, and its periphery. Therefore, the fact itself of limiting the light receiving area by sandwiching the active layer 15 and cladding layers 21, 26 with the metal layers 23, 28, does not lead to a significant decrease in the output signal voltage $v_s$ in Formula (2).

For that reason, the fact of eliminating influence from the substrate 10 and the like by the metal layers 23, 28, and limiting the light receiving area only to the cross section of the active layer 15 and the cladding layers 21, 26 in the first end face 20a, contributes to improvement of the specific detectivity D*. The reason of the fact that a sufficient signal intensity can be obtained even when the light receiving area for the light to be detected is limited to a size of, for example, a few tens of $\mu m^2$, in this way, is because the light to be detected can be used for light detection with high efficiency while being propagated inside the active layer 15 with the waveguide structure using the cladding layers 21, 26, as described above.

Figure 11:
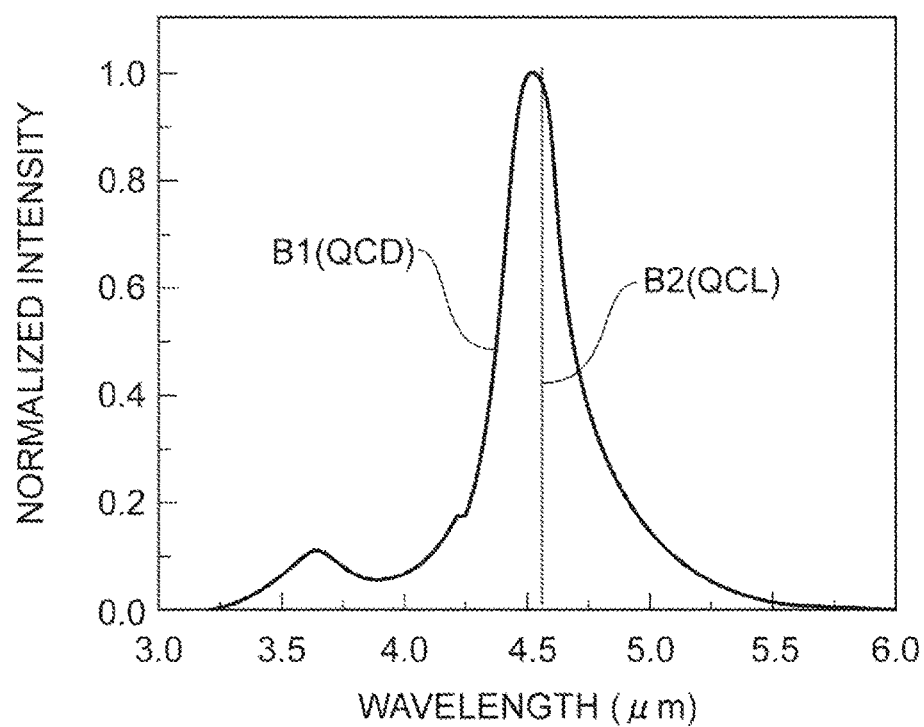
FIG. 11 is a graph showing a sensitivity spectrum in the quantum cascade detector, and an oscillation spectrum in a quantum cascade laser.

FIG. 11 is a graph showing a sensitivity spectrum in the quantum cascade detector 1A, and an oscillation spectrum in a quantum cascade laser. In the graph of FIG. 11, the horizontal axis shows a wavelength (μm), and the vertical axis shows a normalized intensity. In FIG. 11, the graph B1 shows a sensitivity spectrum in the quantum cascade detector (QCD), and the graph B2 shows an oscillation spectrum in the quantum cascade laser (QCL).

As shown in FIG. 11, in the sensitivity spectrum of the quantum cascade detector, the sensitivity wavelength range is about ±0.5 around a wavelength 4.5 μm being the peak of the sensitivity. In FIG. 11, the oscillation spectrum is also shown of the distributed feedback type quantum cascade laser (DFB-QCL) of an oscillation wavelength of 4.6 μm.

A configuration of an optical system and the like using the quantum cascade detector of the above configuration will be described. The quantum cascade detector is preferably used in combination with the quantum cascade laser. In this case, the sensitivity wavelength of the detector can be designed in accordance with the oscillation wavelength of the laser to be used. Since the quantum cascade detector has detection sensitivity only to a wavelength range determined by energy fluctuations of intersubband transitions, it is possible to cut off influence of unnecessary background light without using a filter and the like.

Laser light to be supplied from a laser light source such as the quantum cascade laser can be condensed to a spot size of about a few tens of μm easily by a lens. Therefore, most of the light of the light to be detected can be introduced to the inside of the detector 1A by light condensing using the lens even for the light receiving portion limited to the active layer 15 and cladding layers 21, 26 as described above.

Figure 12:
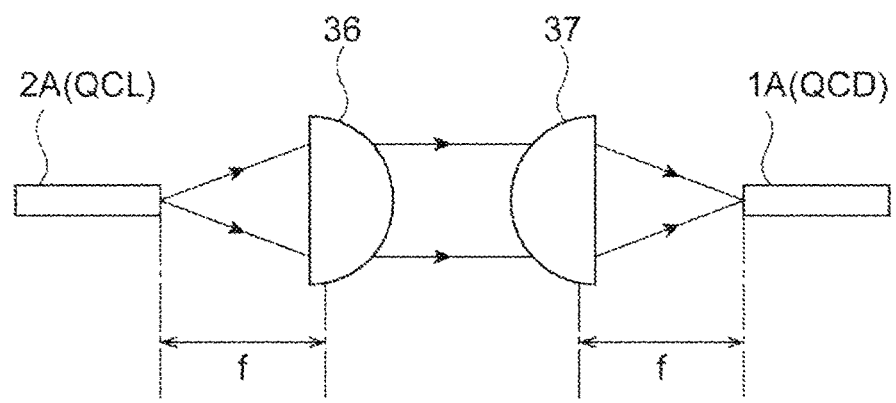
FIG. 12 is a diagram showing an example of a configuration of an optical system including the quantum cascade laser and the quantum cascade detector.

FIG. 12 is a diagram showing an example of a configuration of an optical system including the quantum cascade laser and the quantum cascade detector. In the configuration example shown in FIG. 12, light emitted from a quantum cascade laser 2A is collimated by a lens 36, and the collimated light is condensed by a lens 37 to the light receiving surface of the quantum cascade detector 1A. In this case, the focal lengths of the lenses 36, 37 may be the same as each other, or may be different from each other.

In the above configuration example, the antireflection film is preferably formed on each of the lenses 36, 37 to have reflectance of 5% or less for the light of a wavelength of 4 to 10 μm. As for the material of the lens, any materials may be used having permeability to mid-infrared light, such as ZnSe, $CaF_2$, Ge. The diameter and focal length and the like of the lens are not particularly restricted, however, since there is about 50° of one side spread of radiation light from the quantum cascade laser 2A, the numerical aperture of the lens is preferably 0.5 or more.

Figure 13:
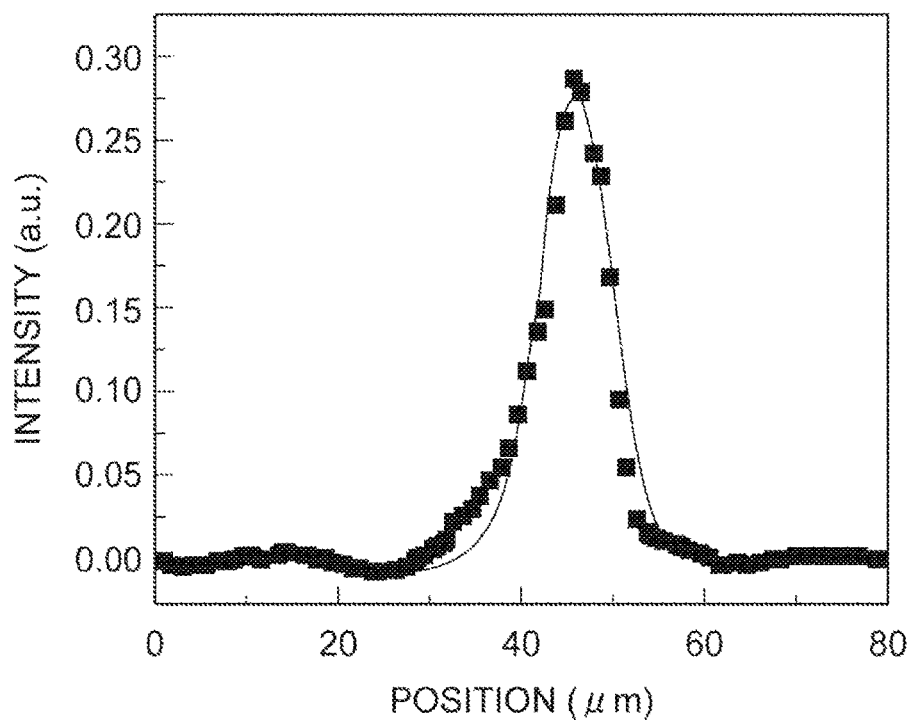
FIG. 13 is a graph showing a light condensing state by a lens of light emitted from the quantum cascade laser.

FIG. 13 is a graph showing a light condensing state by a lens of light emitted from the quantum cascade laser. In the graph of FIG. 13, the horizontal axis shows a position (μm), and the vertical axis shows a light condensing intensity (a.u.). In FIG. 13, the plot points show measurement values, and the solid line shows a fitting curve by Gaussian function.

In FIG. 13, a ZnSe-made aspherical lens of a focal length of 50.8 mm, and a numerical aperture of 0.5 is used as each of the two lenses 36, 37, and FIG. 13 shows the light condensing diameter when the radiation light is condensed from the DFB-QCL of a wavelength of 4.6 μm. A knife-edge method is used for measurement, and the measurement is performed at a position of the light receiving surface in the quantum cascade detector. According to the fitting result by Gaussian function, a full width at half maximum is about 10 μm.

In the quantum cascade detector 1A of the configuration example described above, the sum of the layer thicknesses of the active layer 15 and the cladding layers 21, 26 sandwiched by the metal layers 23, 28 is 7.65 Therefore, regarding the thickness direction of the active layer 15, the receivable range is 70% or more to the full width at half maximum of the condensed light to be detected. Regarding a direction perpendicular to the thickness direction, since the ridge width of the mesa portion 20 is 50 μm, the condensed light to be detected can be all introduced to the inside of the detector 1A, in the direction.

The radiation light from the quantum cascade laser 2A has linear polarization in which the electric field oscillates in a direction perpendicular to the crystal growth surface. For this reason, at the time of incidence of the light to be detected to the quantum cascade detector 1A, the polarization direction is aligned so that the electric field oscillates perpendicularly to the crystal growth surface of the detector 1A similarly, whereby polarization dependency in the quantum cascade detector 1A does not become a problem, and the light form the quantum cascade laser 2A can be efficiently detected.

Here, the light source used in combination with the quantum cascade detector 1A of the above configuration is not limited to the quantum cascade laser, and any light source may be used as far as it radiates mid-infrared light and generates radiation light having a polarization component to which the quantum cascade detector 1A responds, for example, a gas laser such as a carbon dioxide laser, a free electron laser, an infrared semiconductor LED light source, or a black body light source.

Figure 14:
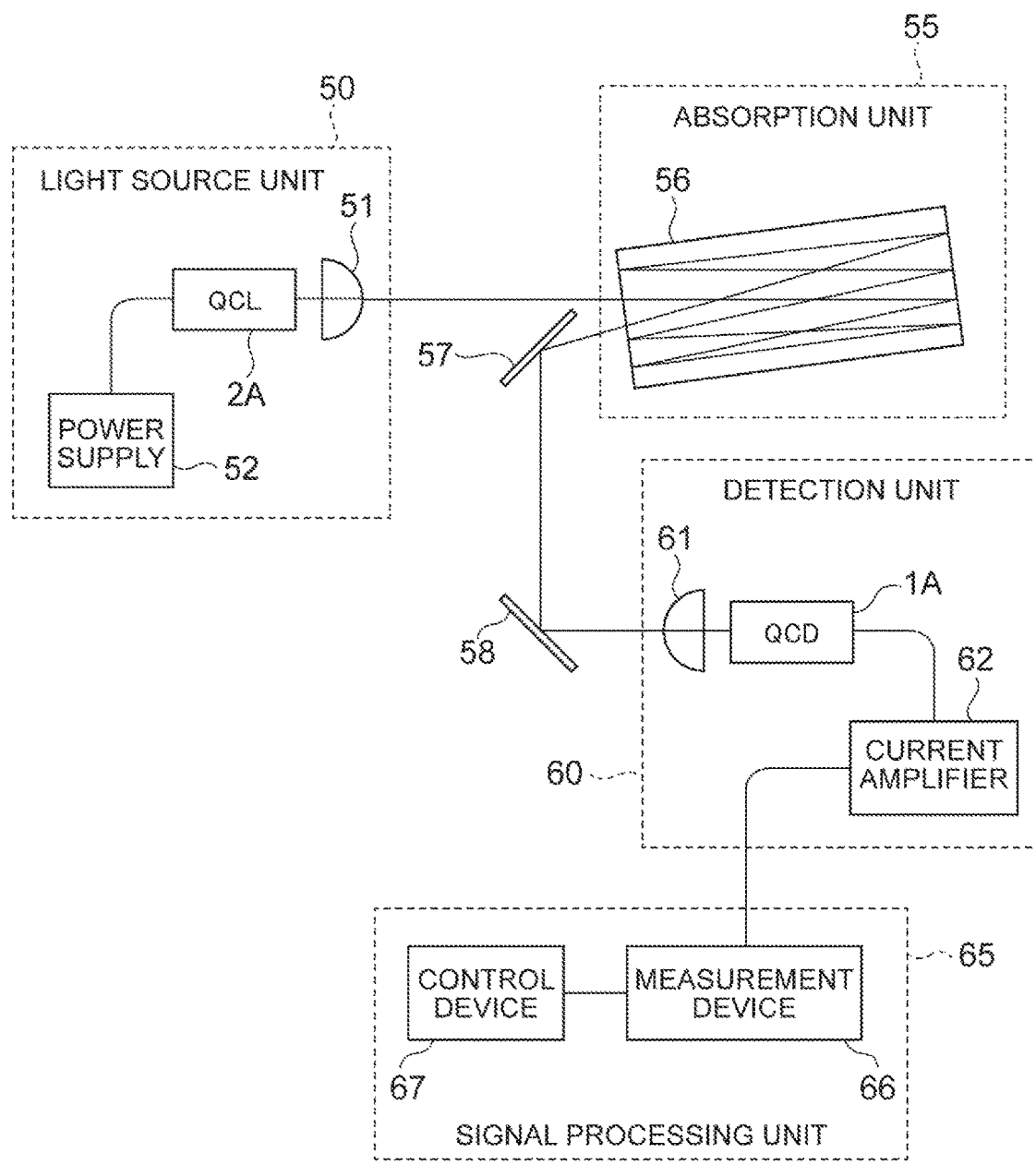
FIG. 14 is a diagram showing another example of the configuration of the optical system including the quantum cascade laser and the quantum cascade detector.

As an example of measurement using the quantum cascade detector 1A of the above configuration, spectrometry of carbon monoxide (CO) will be described. FIG. 14 is a diagram showing another example of the configuration of the optical system including the quantum cascade laser and the quantum cascade detector, and shows a configuration example of a measurement system for performing spectrometry of CO.

The spectrometry system shown in FIG. 14 includes a light source unit 50 including the quantum cascade laser 2A, a power supply 52 of the laser, and a lens 51, an absorption unit 55 including a multipath cell 56, a detection unit 60 including the quantum cascade detector 1A, a lens 61, and a current amplifier 62, and a signal processing unit 65 including a measurement device 66, and a control device (PC) 67. Mirrors 57, 58 are provided between the multipath cell 56 and the lens 61.

In the present configuration example, the light of a wavelength of 4.6 μm emitted from the distributed feedback quantum cascade laser 2A is made to be parallel light by the collimating lens 51, and is caused to enter the multipath cell 56 being a gas cell. The light passing through the gas cell and reflected by the mirrors 57, 58 is condensed by the lens 61, and is caused to enter the quantum cascade detector 1A as the light to be detected, and then a detection signal output from the detector 1A is acquired.

The detection signal acquired in the detector 1A is measured by the measurement device 66 such as an oscilloscope via the current amplifier 62, and presence is observed of absorption of light in CO to be measured by attenuation of the detection signal intensity. In the present configuration example, the multipath cell 56 in which an optical path length is, for example, 100 m is used as a gas cell for measurement; however, not limited to this configuration, depending on a condition such as a gas type to be measured or its concentration, a gas cell of a single path, or a resonator type configuration in which high reflection mirrors are arranged to face each other (for example, CRDS: cavity ring down spectroscopy, ICOS: integrated cavity output spectroscopy), and the like may be used.

Figure 15:
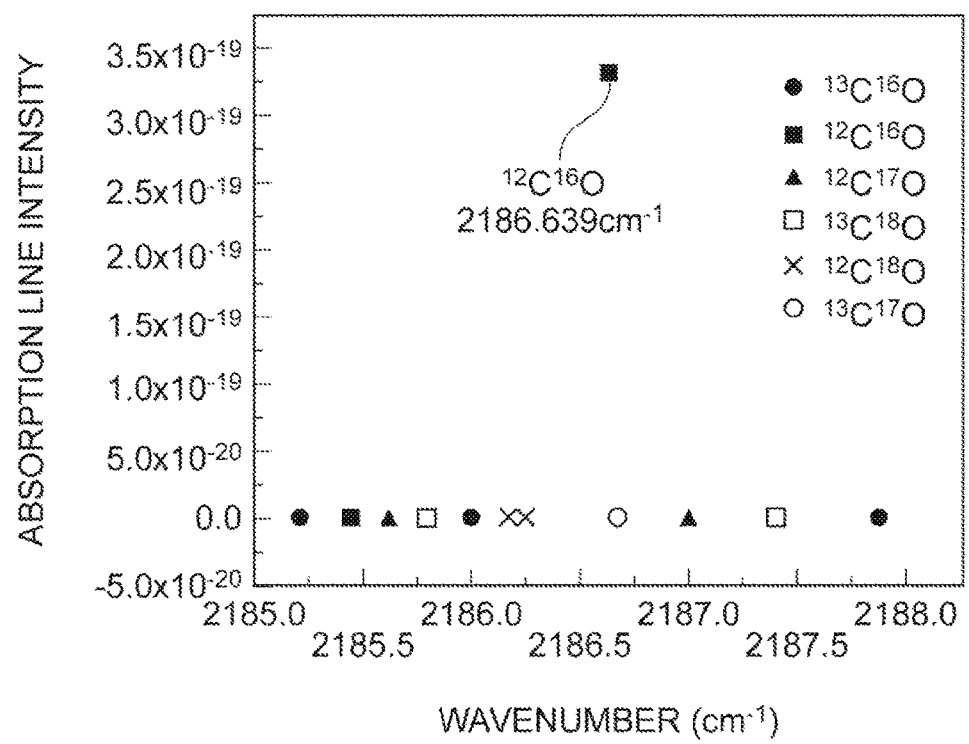
FIG. 15 is a graph showing absorption lines of carbon monoxide (CO).

FIG. 15 is a graph showing absorption lines of carbon monoxide (CO). In the graph of FIG. 15, the horizontal axis shows a wavenumber ($cm^{-1}$), and the vertical axis shows an absorption line intensity. Here, the absorption lines given in HITRAN database are shown. From the data shown in FIG. 15, $^{12}C^{16}O$ having absorption at a wavenumber of 2186.639 $cm^{-1}$ (wavelength of 4.573 μm) is an observation object of light absorption. In the present example, a gas cell of a volume of 0.35 $m^3$ is vacuumed, and CO is sealed inside the gas cell so that the pressure becomes 0.3 Torr. Here, regarding the quantum cascade laser 2A, its temperature is preferably kept constant by a temperature control function. The quantum cascade laser 2A is a single mode oscillation DFB-QCL, and the laser of an oscillation wavelength of 4.6 μm is used in the present example.

Figure 16:
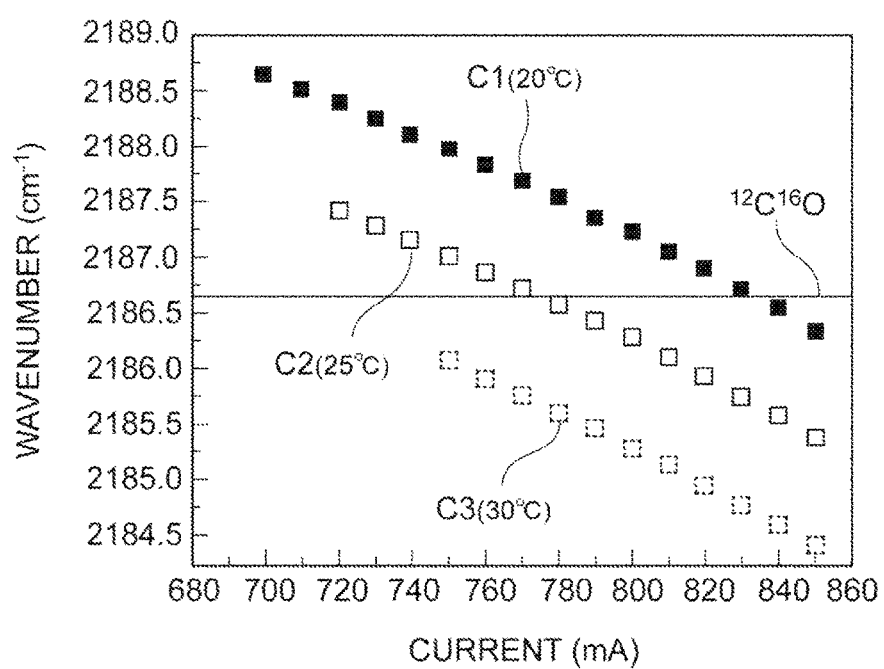
FIG. 16 is a graph showing change of a wavenumber of light by a temperature of the quantum cascade laser, and an injection current.

FIG. 16 is a graph showing change of a wavenumber of light by a temperature of the quantum cascade laser, and an injection current. In the graph of FIG. 16, the horizontal axis shows a current (mA), and the vertical axis shows a wavenumber of light ($cm^{-1}$). In FIG. 16, plot points C1 show current dependency of a wavenumber at a temperature of 20° C., plot points C2 show current dependency of a wavenumber at a temperature of 25° C., and plot points C3 show current dependency of a wavenumber at a temperature of 30° C.

The straight line in FIG. 16 shows the absorption line of CO being the observation object described above. From the graph of FIG. 16, for example, the drive temperature of the quantum cascade laser is 20° C., and the injection current is changed in a range of 830 to 840 mA and the wavelength is continuously scanned, whereby absorption of CO described above can be observed.

Figure 17:
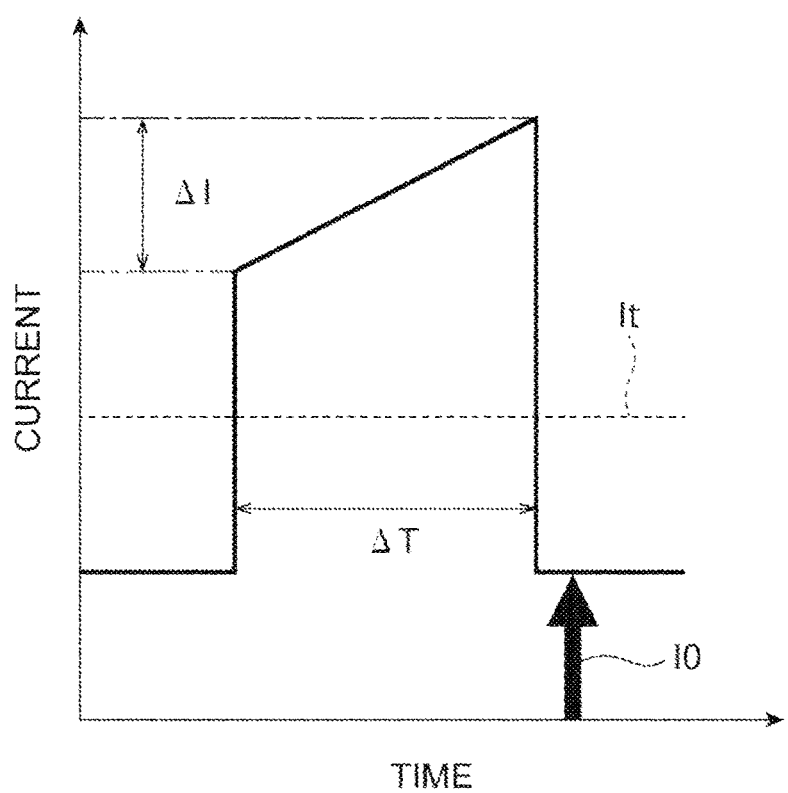
FIG. 17 is a graph showing a spectrometry method using the optical system shown in FIG. 14.

FIG. 17 is a graph showing a spectrometry method using the optical system shown in FIG. 14. As shown in FIG. 17, to the quantum cascade laser, a DC current 10 is injected at a slightly lower value than a threshold value It, and further, modulation is performed with a time width of, for example, ΔT=5 ms by using a function generator from the outside, whereby the wavelength scan described above can be performed. In FIG. 17, a change range of current ΔI is set so that the oscillation wavelength in the quantum cascade laser passes through the absorption line of CO being the observation object. Then, oscillation of the laser is synchronized with the oscilloscope, whereby a valley of attenuation due to absorption of CO can be observed in a pulse signal measured by the oscilloscope.

Figure 18:
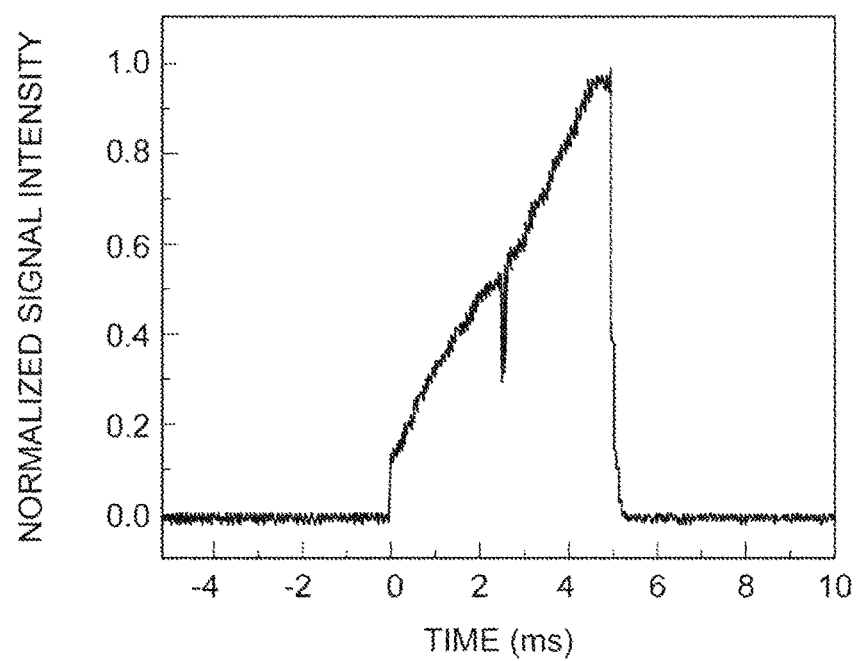
FIG. 18 is a graph showing a result of spectrometry using the optical system shown in FIG. 14.

FIG. 18 is a graph showing a result of spectrometry of CO using the optical system shown in FIG. 14. In the graph of FIG. 18, the horizontal axis shows time (ms), and the vertical axis shows a normalized signal intensity. Here, the quantum cascade detector at room temperature is used for measurement, and integration of 100 measurement results is shown, in spectrometry using the above oscilloscope. As shown in FIG. 18, it can be seen that a sufficient signal intensity is obtained capable of observing the absorption line of CO even in room temperature drive, by using the quantum cascade detector 1A having the above configuration.

As for the quantum cascade detector having the above configuration, for example, it is possible to configure the detector array by arranging a plurality of quantum cascade detectors in one-dimensional array along a predetermined array direction.

Figure 19:
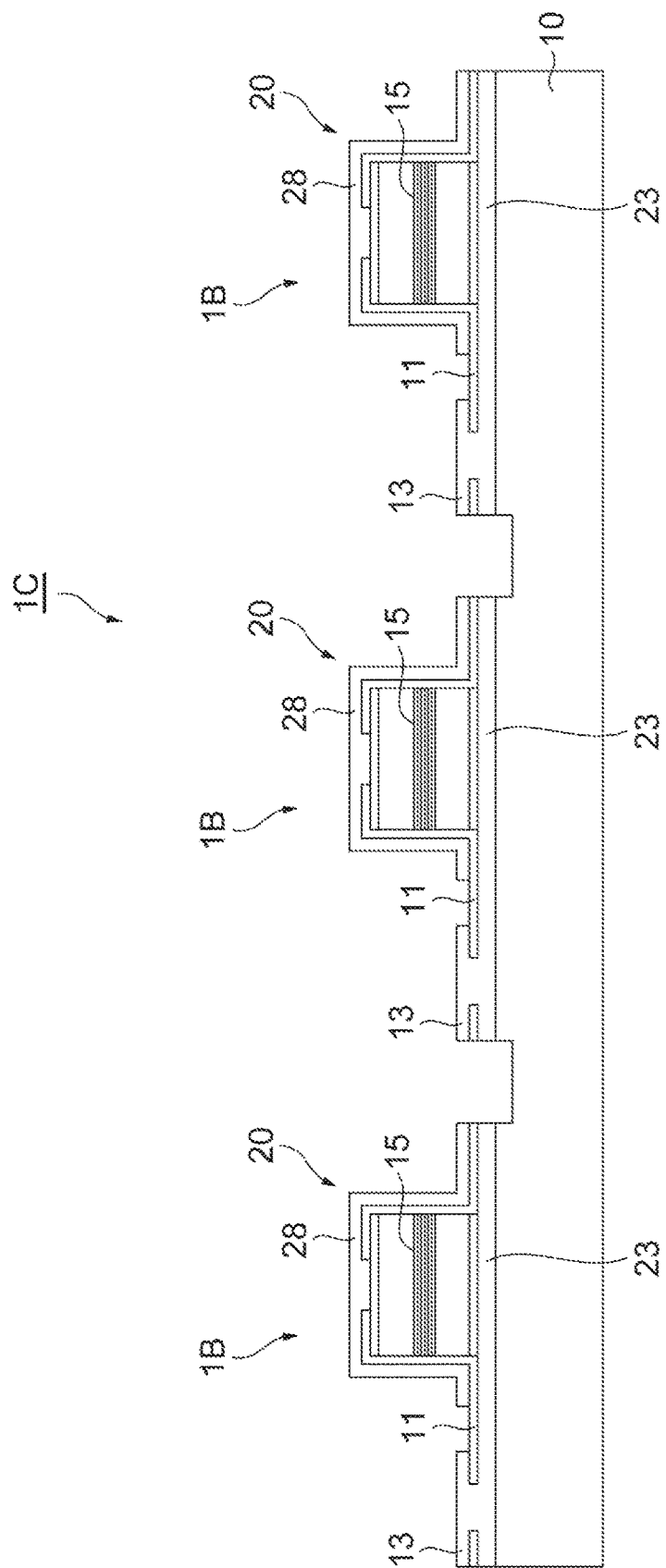
FIG. 19 is a front cross-sectional view showing an example of a configuration of a detector array using the quantum cascade detector.

FIG. 19 is a front cross-sectional view showing an example of a configuration of a detector array using the quantum cascade detector. In the configuration example shown in FIG. 19, the quantum cascade detector 1B of the configuration shown in FIG. 5 is used as the quantum cascade detector. A detector array 1C is configured so that the array direction is a direction perpendicular to the waveguide direction in the waveguide structure in the detector 1B, and a plurality of (in the figure, three) quantum cascade detectors 1B are arrayed in a one-dimensional array along the array direction on the semiconductor substrate 10. This detector array 1C can be used as a line sensor, for example.

An example of a method for manufacturing the detector array 1C using the quantum cascade detectors 1B according to the above configuration example will be described briefly. First, similarly to the method for manufacturing the quantum cascade detector 1A described above, the contact layer, the cladding layer, the active layer, the cladding layer, and the contact layer are caused to grow on the InP substrate (first substrate), and further thereon, the first metal layer made of Au is deposited. Next, the second metal layer made of Au is deposited on the semi-insulating InP substrate (second substrate) to be the semiconductor substrate 10, and the first metal layer on the first substrate and the second metal layer on the second substrate are brought into contact with each other and subjected to heat treatment with a moderate load, whereby the two substrates are bonded together. The first, second metal layers bonded become the lower metal layer 23 on the substrate 10.

After that, the first substrate used for growth of the semiconductor laminate structure is removed by selective chemical etching, and further, the stripe-shaped mesa structure is formed by wet etching or dry etching. In addition, the insulating layer 11 made of an insulating material such as SiN is formed, and the openings 11a, 11b (see FIG. 5) are formed, and the upper metal layer 28 made of Au or the like to be the upper electrode layer and the lower electrode layer 13 made of Au or the like are formed.

Subsequently, as shown in FIG. 19, the metal layer and the like are removed by etching up to the substrate 10 at a predetermined position between the adjacent detectors 1B so that the plurality of quantum cascade detectors 1B arrayed on the semiconductor substrate 10 are electrically separated from each other. Finally, cleavage is performed so that a predetermined device length is obtained, and the device is divided while keeping a state in which the plurality of detectors 1B are arranged in an array, whereby the detector array 1C functioning as the line sensor is manufactured.

On the second end face (reflection surface) of the waveguide structure in each of the quantum cascade detectors 1B constituting the detector array 1C, for example, the reflection film (high reflection coat) is formed whose reflectance is 95% or more for the light of the wavelength of the light to be detected. Meanwhile, on the first end face (entrance surface), in order to suppress reflection at the cleavage plane, for example, the antireflection film (antireflection coat) is formed whose reflectance is 28% or less for the light of the wavelength of the light to be detected.

The stripe width, the stripe interval, and the like of each of the detectors 1B in the detector array 1C depend on the mask pattern in the photolithography. The configuration conditions of the detector array 1C can be appropriately set depending on a spatial resolution required as the line sensor, for example. Necessary wiring is performed to each of the quantum cascade detectors 1B arrayed on the semiconductor substrate 10, and the detectors are connected to readout circuits, whereby the detector array 1C can be served as the line sensor.

The line sensor according to the above configuration example can be used as a photodetector for a spectroscope, for example. In this case, light components are detected for each wavelength by using the line sensor of the above configuration, for the light to which spectral decomposition is performed by a spectroscopic element such as a diffraction grating or a prism, whereby the optical spectrum can be obtained in a simple manner.

In application to the spectroscope of the line sensor, high spatial resolution is required in the line sensor being the photodetector, in order to obtain continuous spectrum information. In the detector array 1C of the above configuration, the stripe width, the stripe interval, and the like of each of the detectors 1B can be controlled by the mask pattern in the photolithography as described above, therefore, the spatial resolution of light detection can be easily increased by reducing the stripe width and the interval.

Increasing the spatial resolution by narrowing the stripe width in the quantum cascade detectors 1B corresponds to a reduction of the light receiving area, and leads to a reduction in the signal intensity in each of the detectors 1B separated. On the other hand, according to the above configuration in which the light to be detected is guided by the waveguide structure in the detector 1B and absorbed by the active layer 15, photoelectric current can be efficiently obtained even for the light to be detected of a feeble amount of incident light.

The quantum cascade detector according to the present invention is not limited to the above-described embodiments and configuration examples, and can be variously modified. For example, in the above-described configuration example, an example has been shown in which the InP substrate is used as the semiconductor substrate, and the active layer is configured by InGaAs/InAlAs, however, various configuration can be used for the structure of the active layer, specifically. As for the semiconductor material systems, various material systems can be used, such as AlGaAs/GaAs, InGaN/GaN, besides the above-described InGaAs/InAlAs. As for the semiconductor material constituting the cladding layer, an appropriate material can be used in accordance with the semiconductor material system and the like of the active layer.

In the above-described configuration example, the quantum cascade detector is configured in the mesa structure having the base portion including the semiconductor substrate, and the mesa portion including the active layer, however, not limited to this configuration, a structure other than the mesa structure may be used. As for the antireflection film on the first end face and the reflection film on the second end face in the waveguide structure, a configuration may be used in which the films are not provided if not necessary, or a configuration may be used in which only one of the films is provided.

In the quantum cascade detector of the above configuration, the active layer is provided with the lower cladding layer, and the upper cladding layer, and the reflection film for increasing reflectance for the light to be detected is formed on the second end face being at the opposite side to the first end face to be the entrance surface for the light to be detected in the waveguide structure with the active layer and the lower, upper cladding layers. This configuration is also effective in a configuration in which the lower, upper metal layers are not provided. In this case, the antireflection film is more preferably formed for reducing reflectance for the light to be detected, on the first end face.

The quantum cascade detector according to the above embodiments is configured to include: (1) a semiconductor substrate; (2) an active layer provided on the semiconductor substrate and having a cascade structure in which absorption regions and transport regions are alternately stacked in the form of a multistage lamination of unit laminate structures each of which includes n (where n is an integer of 3 or more) quantum well layers including a first well layer serving as an absorption well layer and n quantum barrier layers, the absorption region including the first well layer and detecting light to be detected by intersubband absorption, the transport region transporting electrons excited by the intersubband absorption; (3) a lower cladding layer provided between the active layer and the semiconductor substrate and having a lower refractive index than the active layer; (4) a lower metal layer provided between the lower cladding layer and the semiconductor substrate; (5) an upper cladding layer provided on an opposite side to the semiconductor substrate for the active layer and having a lower refractive index than the active layer; and (6) an upper metal layer provided on an opposite side to the active layer for the upper cladding layer, and, (7) of a first end face and a second end face being in a waveguide direction in a waveguide structure with the active layer, the lower cladding layer, and the upper cladding layer, the first end face is an entrance surface for the light to be detected.

Here, as for the layer thickness of each semiconductor layer constituting the quantum cascade detector, each of the lower cladding layer and the upper cladding layer preferably has a layer thickness of 2 μm or more and 10 μm or less. The active layer preferably has a layer thickness of 1 μm or more. According to these configurations, it is possible to suitably achieve the waveguide structure for the light to be detected by the active layer and the cladding layers, the light confinement structure in the waveguide, and the like.

In each of the lower cladding layer and the upper cladding layer, the impurity doping density is preferably $5 \times 10^{16}$ cm$^{-3}$ or more and $2 \times 10^{17}$ cm$^{-3}$ or less. According to this configuration, by the setting of the doping density in the cladding layer, series resistance in the detector can be reduced, and loss of the light in the cladding layer can be suppressed.

In the active layer, the impurity doping density is preferably $1\times10^{17}$ cm$^{-3}$ or more and $9\times10^{17}$ cm$^{-3}$ or less. According to this configuration, it is possible to suitably achieve the waveguide structure with the active layer and the cladding layers, the light confinement structure, the light detection structure in the active layer, and the like.

The quantum cascade detector may be configured in a mesa structure having a base portion including the semiconductor substrate; and a mesa portion provided on the base portion and including the active layer, and extending in a stripe shape in the waveguide direction in the waveguide structure. According to this configuration, the waveguide structure with the active layer and the cladding layers can be suitably configured along the mesa portion.

The quantum cascade detector may have a configuration in which an antireflection film for reducing reflectance for the light to be detected is formed on the first end face being the entrance surface for the light to be detected in the waveguide structure. According to this configuration, incident efficiency is improved of the light to be detected from the entrance surface to the inside of the detector, whereby detection efficiency of the light in the detector can be improved.

The quantum cascade detector may have a configuration in which a reflection film for increasing reflectance for the light to be detected is formed on the second end face in the waveguide structure, and the second end face is a reflection surface for the light to be detected. According to this configuration, the light to be detected guided from the entrance surface through the waveguide structure and reaching the reflection surface is returned to the inside of the detector again, whereby detection efficiency of the light in the detector can be improved.

The present invention can be used as a quantum cascade detector capable of detecting the light to be detected with high efficiency.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A quantum cascade detector comprising:
a semiconductor substrate;
an active layer provided on the semiconductor substrate and having a cascade structure in which absorption regions and transport regions are alternately stacked in the form of a multistage lamination of unit laminate structures each of which comprises n (where n is an integer of 3 or more) quantum well layers including a first well layer serving as an absorption well layer and n quantum barrier layers, the absorption region including the first well layer and detecting light to be detected by intersubband absorption, the transport region transporting electrons excited by the intersubband absorption;
a lower cladding layer provided between the active layer and the semiconductor substrate and having a lower refractive index than the active layer;
a lower metal layer provided between the lower cladding layer and the semiconductor substrate;
an upper cladding layer provided on an opposite side to the semiconductor substrate with respect to the active layer and having a lower refractive index than the active layer; and
an upper metal layer provided on an opposite side to the active layer with respect to the upper cladding layer, wherein
a waveguide structure is configured with the active layer, the lower cladding layer, and the upper cladding layer so as to guide the light to be detected along the active layer, and the waveguide structure is sandwiched by the lower metal layer and the upper metal layer, and
of a first end face and a second end face being in a waveguide direction of the light to be detected in the waveguide structure, the first end face including cross sections of the active layer, the lower cladding layer, and the upper cladding layer is an entrance surface from which the light to be detected enters.

2. The quantum cascade detector according to claim 1, wherein each of the lower cladding layer and the upper cladding layer has a layer thickness of 2 μm or more and 10 μm or less.

3. The quantum cascade detector according to claim 1, wherein the active layer has a layer thickness of 1 μm or more.

4. The quantum cascade detector according to claim 1, wherein each of the lower cladding layer and the upper cladding layer has a doping density of impurities of $5\times10^{16}$ cm$^{-3}$ or more and $2\times10^{17}$ cm$^{-3}$ or less.

5. The quantum cascade detector according to claim 1, wherein the active layer has a doping density of impurities of $1\times10^{17}$ cm$^{-3}$ or more and $9\times10^{17}$ cm$^{-3}$ or less.

6. The quantum cascade detector according to claim 1, being configured in a mesa structure having a base portion including the semiconductor substrate; and a mesa portion provided on the base portion, including the active layer, and extending in a stripe shape in the waveguide direction in the waveguide structure.

7. The quantum cascade detector according to claim 1, wherein an antireflection film for reducing reflectance for the light to be detected is formed on the first end face in the waveguide structure.

8. The quantum cascade detector according to claim 1, wherein a reflection film for increasing reflectance for the light to be detected is formed on the second end face in the waveguide structure, and the second end face is a reflection surface for the light to be detected.

9. The quantum cascade detector according to claim 1, wherein a light receiving area in the entrance surface is limited to the cross sections of the active layer, the lower cladding layer, and the upper cladding layer by the lower metal layer and the upper metal layer.

* * * * *